(12) United States Patent
Bozonet et al.

(10) Patent No.: US 7,439,049 B2
(45) Date of Patent: Oct. 21, 2008

(54) NUCLEIC ACID MOLECULES CODING FOR A DEXTRAN-SACCHARASE CATALYSING THE SYNTHESIS OF DEXTRAN WITH α 1,2 OSIDIC SIDECHAINS

(75) Inventors: Sophie Anne Michèle Bozonet, Gagnac-sur-Garonne (FR); Magali Martine Claude Remaud-Simeon, Ramonville-Saint-Agne (FR); René-Marc Lucien Willemot, Pompertuzat (FR); Pierre Emmanuel Frédéric Monsan, Mondonville (FR)

(73) Assignee: Institut National des Sciences Appliquees (INSA), Toulouse (FR)

( * ) Notice: Subject to any disclaimer, the term of this patent is extended or adjusted under 35 U.S.C. 154(b) by 301 days.

(21) Appl. No.: 10/509,024

(22) PCT Filed: Mar. 18, 2002

(86) PCT No.: PCT/FR02/00951

§ 371 (c)(1),
(2), (4) Date: Sep. 27, 2004

(87) PCT Pub. No.: WO02/074943

PCT Pub. Date: Sep. 26, 2002

(65) Prior Publication Data

US 2006/0210510 A1    Sep. 21, 2006

(30) Foreign Application Priority Data

Mar. 16, 2001 (FR) .................................. 01 03631
Dec. 19, 2001 (FR) .................................. 01 16495

(51) Int. Cl.
*C12N 9/10* (2006.01)
*C12N 9/00* (2006.01)
*C12N 9/12* (2006.01)
*C07H 21/04* (2006.01)

(52) U.S. Cl. .................. 435/193; 435/183; 435/252.3; 435/320.1; 536/23.2

(58) Field of Classification Search ................ 435/183, 435/193, 252.3, 320.1; 536/23.2
See application file for complete search history.

(56) References Cited

U.S. PATENT DOCUMENTS 5,141,858 A * 8/1992 Paul et al. ................ 435/97

FOREIGN PATENT DOCUMENTS

| EP | 0 325 872 A | 8/1989 |
|---|---|---|
| WO | WO-89/12386 A | 12/1989 |
| WO | WO-00/47727 A | 8/2000 |

OTHER PUBLICATIONS

Fabre et al. J Bacteriol. Jan. 2005;187(1):296-303.*
Bhatnagar et al., retrieved from EBI, accession No. Q9ZAR4 (1999).
Bhatnagar et al., retrieved from EBI, accession No. U81374 (1999).
Monchois V et al., Gene, vol. 182, No. 1-2 pp. 23-32 (1996).
Kim D et al., Enzyme and microbial technology, Stoneham, MA, US vol. 17, No. 12, 1995, pp. 1050-1056.

* cited by examiner

*Primary Examiner*—Tekchand Saidha
*Assistant Examiner*—Christian L Fronda
(74) *Attorney, Agent, or Firm*—Birch, Stewart, Kolasch & Birch, LLP

(57) ABSTRACT

The invention relates to an isolated polypeptide with an glycosyl transferase enzymatic activity for producing dextrans with α(1→2) sidechains, comprising at least one region for bonding to glucan and a catalytically active region situated beyond the region bonding to glucan. The invention further relates to polynucleotides coding for said enzymes and vectors containing the same.

14 Claims, 6 Drawing Sheets

Figure 1:
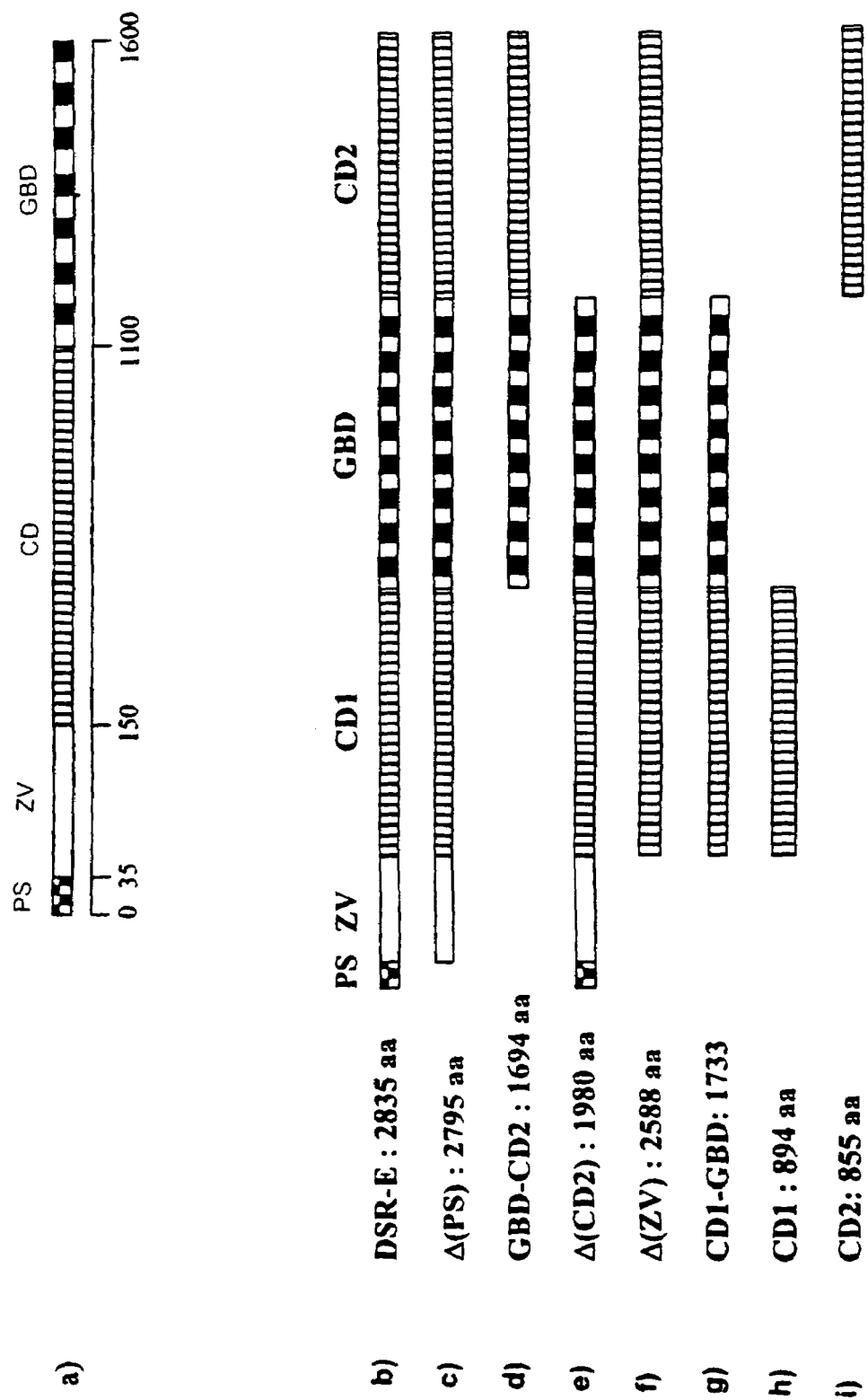

⁷³AAKVVAVATTP-AT
⁸⁶PVADKTVSA
⁹⁵PAADKAVDTTSSTT
¹⁰⁹PATDKAVDTTP-TT
¹²²PAADKAVDTTP-TT
¹³⁵PAADKAVDTTP-TT
¹⁴⁸PAANKAVDTTP-AT
¹⁶¹AATDKAV-ATP-AT
¹⁷³PAADKLANTT--AT
¹⁸⁵----DKAVATTP-AT
¹⁹⁶PVANKAA

PAADKAVDTTP-A/T T  ← Proposed consensus sequence for S repeat

```
GTFB   341  SAWNSDSEK----PFDDHLQN      402  GGYEFLLANDVDNSNPVVQAEQLN
GTFI   341  PQWNGESEK----PYDDHLQN      404  GGYELLLANDVDNSNPIVQAEQLN
GTFS   327  NQWSIASENETVYPNQDHMQG      388  AGYELLLANDVDNSNPVVQAEQLN
dsrS   444  PQWNETSED----MSNDHLQN      502  GGFELLLANDVDNSNPVVQAEQLN
dsrA   181  PNWNIDSEA----KGDDHLQG      237  GGFELLLANDVDNSNPVVQAEQLN
dsrB   426  PQWNMSSED----PKNDHLQN      484  GGFELLLANDVDNSNPVVQSEQLN
asr    525  ANWNKQTEDEAF-DGLQWLQG      585  KGSEFLLANDIDNSNPIVQAEQLN
CD1    423  ANWNIDSES----KGNDHLQG      478  GGYEMLLANDVDNSNPVVQAEQLN
CD2   2120  FIWNKDSEYHG--GGDAWFQG     2161  NAFDFLLANDVDNSNPVVQAENLN
                  *.  :*                       .  ::******:*****:*;***
```

B

C

```
GTFB   443  ANFDSIRVDAVDNVDADLLQI      484  HLSILEAWSDND
GTFI   445  ANFDSIRVDAVDNVDADLLQI      486  HVSIVEAWSDND
GTFS   429  ANFDGVRVDAVDNVDADLLQI      470  HLSILEAWSGND
dsrS   543  ANFDGIRVDAVDNVDADLLQI      584  HLSILEDWSHND
dsrA   278  ANFDGYRVDAVDNVDADLLQI      319  IYQFWKTGEMKI
dsrB   525  ANFDGIRVDAVDNVDADLLQI      566  HLSILEDWSHND
asr    626  ANFDGIRVDAVDNVDADLLKI      667  HLSILEDWNGKD
CD1    519  ANFDGYRVDAVDNVDADLLQI      560  HISILEDWDNND
CD2   2202  ANFDSIRIDAVDFIHNDTIQR     2243  HISLVEAG----
            ****.:*:******  . * ::            .: ::
```

D

E

```
GTFB   555  YSFIRAHDSEVQDLI      928  DWVPDQMY
GTFI   557  YSFARAHDSEVQDLI      932  DWVPDQMY
GTFS   540  YVFIRAHDSEVQTRI      915  DLVPNQLY
dsrS   655  YSFIRAHDSEVQTVI     1024  DWVPDQIY
dsrA   390  YSFVRAHDSEVQTII      765  DWVPDQIY
dsrB   637  YSFVRAHDSEVQTVI     1005  DWVPDQIY
asr    759  YSFVRAHDYDAQDPI     1168  DWVPDQIY
CD1    631  YAFIRAHDSEVQTVI     1014  DWVPDQIY
CD2   2315  YSIIHAHDKGVQEKV     2689  DVVDNQVY
            * :: **** . .                * * .:*;*
```

F

SEQUENCE LISTING

```
<160> NUMBER OF SEQ ID NOS: 103

<210> SEQ ID NO 1
<211> LENGTH: 855
<212> TYPE: PRT
<213> ORGANISM: Leuconostoc mesenteroides
<220> FEATURE:
<223> OTHER INFORMATION: catalytic domain

<400> SEQUENCE: 1

Asp Met Ser Thr Asn Ala Phe Ser Thr Lys Asn Val Ala Phe Asn His
 1               5                  10                  15

Asp Ser Ser Ser Phe Asp His Thr Val Asp Gly Phe Leu Thr Ala Asp
                20                  25                  30

Thr Trp Tyr Arg Pro Lys Ser Ile Leu Ala Asn Gly Thr Thr Trp Arg
            35                  40                  45

Asp Ser Thr Asp Lys Asp Met Arg Pro Leu Ile Thr Val Trp Trp Pro
        50                  55                  60

Asn Lys Asn Val Gln Val Asn Tyr Leu Asn Phe Met Lys Ala Asn Gly
    65                  70                  75                  80

Leu Leu Thr Thr Ala Ala Gln Tyr Thr Leu His Ser Asp Gln Tyr Asp
                85                  90                  95

Leu Asn Gln Ala Ala Gln Asp Val Gln Val Ala Ile Glu Arg Arg Ile
                100                 105                 110

Ala Ser Glu His Gly Thr Asp Trp Leu Gln Lys Leu Leu Phe Glu Ser
            115                 120                 125

Gln Asn Asn Asn Pro Ser Phe Val Lys Gln Gln Phe Ile Trp Asn Lys
        130                 135                 140

Asp Ser Glu Tyr His Gly Gly Gly Asp Ala Trp Phe Gln Gly Gly Tyr
    145                 150                 155                 160

Leu Lys Tyr Gly Asn Asn Pro Leu Thr Pro Thr Thr Asn Ser Asp Tyr
                165                 170                 175

Arg Gln Pro Gly Asn Ala Phe Asp Phe Leu Leu Ala Asn Asp Val Asp
                180                 185                 190

Asn Ser Asn Pro Val Val Gln Ala Glu Asn Leu Asn Trp Leu His Tyr
            195                 200                 205
```

-continued

```
Leu Met Asn Phe Gly Thr Ile Thr Ala Gly Gln Asp Ala Asn Phe
    210                 215                 220

Asp Ser Ile Arg Ile Asp Ala Val Asp Phe Ile His Asn Asp Thr Ile
225                 230                 235                 240

Gln Arg Thr Tyr Asp Tyr Leu Arg Asp Ala Tyr Gln Val Gln Gln Ser
                245                 250                 255

Glu Ala Lys Ala Asn Gln His Ile Ser Leu Val Glu Ala Gly Leu Asp
                260                 265                 270

Ala Gly Thr Ser Thr Ile His Asn Asp Ala Leu Ile Glu Ser Asn Leu
            275                 280                 285

Arg Glu Ala Ala Thr Leu Ser Leu Thr Asn Glu Pro Gly Lys Asn Lys
    290                 295                 300

Pro Leu Thr Asn Met Leu Gln Asp Val Asp Gly Thr Leu Ile Thr
305                 310                 315                 320

Asp His Thr Gln Asn Ser Thr Glu Asn Gln Ala Thr Pro Asn Tyr Ser
                325                 330                 335

Ile Ile His Ala His Asp Lys Gly Val Gln Glu Lys Val Gly Ala Ala
                340                 345                 350

Ile Thr Asp Ala Thr Gly Ala Asp Trp Thr Asn Phe Thr Asp Glu Gln
            355                 360                 365

Leu Lys Ala Gly Leu Glu Leu Phe Tyr Lys Asp Gln Arg Ala Thr Asn
    370                 375                 380

Lys Lys Tyr Asn Ser Tyr Asn Ile Pro Ser Ile Tyr Ala Leu Met Leu
385                 390                 395                 400

Thr Asn Lys Asp Thr Val Pro Arg Met Tyr Tyr Gly Asp Met Tyr Gln
                405                 410                 415

Asp Asp Gly Gln Tyr Met Ala Asn Lys Ser Ile Tyr Tyr Asp Ala Leu
                420                 425                 430

Val Ser Leu Met Thr Ala Arg Lys Ser Tyr Val Ser Gly Gly Gln Thr
            435                 440                 445

Met Ser Val Asp Asn His Gly Leu Leu Lys Ser Val Arg Phe Gly Lys
    450                 455                 460

Asp Ala Met Thr Ala Asn Asp Leu Gly Thr Ser Ala Thr Arg Thr Glu
465                 470                 475                 480

Gly Leu Gly Val Ile Ile Gly Asn Asp Pro Lys Leu Gln Leu Asn Asp
                485                 490                 495

Ser Asp Lys Val Thr Leu Asp Met Gly Ala Ala His Lys Asn Gln Lys
                500                 505                 510

Tyr Arg Ala Val Ile Leu Thr Thr Arg Asp Gly Leu Ala Thr Phe Asn
            515                 520                 525

Ser Asp Gln Ala Pro Thr Ala Trp Thr Asn Asp Gln Gly Thr Leu Thr
    530                 535                 540

Phe Ser Asn Gln Glu Ile Asn Gly Gln Asp Asn Thr Gln Ile Arg Gly
545                 550                 555                 560

Val Ala Asn Pro Gln Val Ser Gly Tyr Leu Ala Val Trp Val Pro Val
                565                 570                 575

Gly Ala Ser Asp Asn Gln Asp Ala Arg Thr Ala Ala Thr Thr Thr Glu
                580                 585                 590

Asn His Asp Gly Lys Val Leu His Ser Asn Ala Ala Leu Asp Ser Asn
            595                 600                 605

Leu Ile Tyr Glu Gly Phe Ser Asn Phe Gln Pro Lys Ala Thr His
    610                 615                 620
```

```
Asp Glu Leu Thr Asn Val Val Ile Ala Lys Asn Ala Asp Val Phe Asn
625                 630                 635                 640

Asn Trp Gly Ile Thr Ser Phe Glu Met Ala Pro Gln Tyr Arg Ser Ser
                645                 650                 655

Gly Asp His Thr Phe Leu Asp Ser Thr Ile Asp Asn Gly Tyr Ala Phe
            660                 665                 670

Thr Asp Arg Tyr Asp Leu Gly Phe Asn Thr Pro Thr Lys Tyr Gly Thr
        675                 680                 685

Asp Gly Asp Leu Arg Ala Thr Ile Gln Ala Leu His His Ala Asn Met
    690                 695                 700

Gln Val Met Ala Asp Val Val Asp Asn Gln Val Tyr Asn Leu Pro Gly
705                 710                 715                 720

Lys Glu Val Val Ser Ala Thr Arg Ala Gly Val Tyr Gly Asn Asp Asp
                725                 730                 735

Ala Thr Gly Phe Gly Thr Gln Leu Tyr Val Thr Asn Ser Val Gly Gly
            740                 745                 750

Gly Gln Tyr Gln Glu Lys Tyr Ala Gly Gln Tyr Leu Glu Ala Leu Lys
        755                 760                 765

Ala Lys Tyr Pro Asp Leu Phe Glu Gly Lys Ala Tyr Asp Tyr Trp Tyr
    770                 775                 780

Lys Asn Tyr Ala Asn Asp Gly Ser Asn Pro Tyr Tyr Thr Leu Ser His
785                 790                 795                 800

Gly Asp Arg Glu Ser Ile Pro Ala Asp Val Ala Ile Lys Gln Trp Ser
                805                 810                 815

Ala Lys Tyr Met Asn Gly Thr Asn Val Leu Gly Asn Gly Met Gly Tyr
            820                 825                 830

Val Leu Lys Asp Trp His Asn Gly Gln Tyr Phe Lys Leu Asp Gly Asp
        835                 840                 845

Lys Ser Thr Leu Pro Gln Ile
    850                 855

<210> SEQ ID NO 2
<211> LENGTH: 2835
<212> TYPE: PRT
<213> ORGANISM: Leuconostoc mesenteroides
<220> FEATURE:
<223> OTHER INFORMATION: Complete protein DSR-E

<400> SEQUENCE: 2

Met Arg Asp Met Arg Val Ile Cys Asp Arg Lys Lys Leu Tyr Lys Ser
1               5                   10                  15

Gly Lys Val Leu Val Thr Ala Gly Ile Phe Ala Leu Met Met Phe Gly
            20                  25                  30

Val Thr Thr Ala Ser Val Ser Ala Asn Thr Ile Ala Val Asp Thr Asn
        35                  40                  45

His Ser Arg Thr Ser Ala Gln Ile Asn Lys Ser Ala Val Asp Lys Val
    50                  55                  60

Asn Asp Asp Lys Thr Thr Leu Gly Ala Ala Lys Val Val Ala Val Ala
65                  70                  75                  80

Thr Thr Pro Ala Thr Pro Val Ala Asp Lys Thr Val Ser Ala Pro Ala
                85                  90                  95

Ala Asp Lys Ala Val Asp Thr Thr Ser Ser Thr Pro Ala Thr Asp
            100                 105                 110

Lys Ala Val Asp Thr Thr Pro Thr Thr Pro Ala Ala Asp Lys Ala Val
        115                 120                 125
```

```
Asp Thr Thr Pro Thr Thr Pro Ala Ala Asp Lys Ala Val Asp Thr Thr
130                 135                 140

Pro Thr Thr Pro Ala Ala Asn Lys Ala Val Asp Thr Thr Pro Ala Thr
145                 150                 155                 160

Ala Ala Thr Asp Lys Ala Val Ala Thr Pro Ala Thr Pro Ala Ala Asp
        165                 170                 175

Lys Leu Ala Asn Thr Thr Pro Ala Thr Asp Lys Ala Val Ala Thr Thr
            180                 185                 190

Pro Ala Thr Pro Val Ala Asn Lys Ala Ala Asp Thr Ser Ser Ile His
        195                 200                 205

Asp Gln Pro Leu Asp Thr Asn Val Pro Thr Asp Lys Ser Ala Asn Leu
210                 215                 220

Val Ser Thr Thr Gln Lys Ser Thr Asp Asn Gln Gln Val Lys Ser Thr
225                 230                 235                 240

Glu Thr Ser His Leu Gln Glu Ile Asn Gly Lys Thr Tyr Phe Leu Asp
                245                 250                 255

Asp Asn Gly Gln Val Lys Lys Asn Phe Thr Ala Ile Ile Asp Gly Lys
            260                 265                 270

Val Leu Tyr Phe Asp Lys Thr Ser Gly Glu Leu Thr Ala Asn Ala Pro
        275                 280                 285

Gln Val Thr Lys Gly Leu Val Asn Ile Asp Asn Ala His Asn Ala Ala
290                 295                 300

His Asp Leu Thr Ala Asp Asn Phe Thr Asn Val Asp Gly Tyr Leu Thr
305                 310                 315                 320

Ala Asn Ser Trp Tyr Arg Pro Lys Asp Ile Leu Lys Asn Gly Thr Thr
                325                 330                 335

Trp Thr Pro Thr Thr Ala Glu Asp Phe Arg Pro Leu Leu Met Ser Trp
            340                 345                 350

Trp Pro Asp Lys Asn Thr Gln Val Ala Tyr Leu Gln Tyr Met Gln Ser
        355                 360                 365

Val Gly Met Leu Pro Asp Asp Val Lys Val Ser Asn Asp Asp Asn Met
    370                 375                 380

Ser Thr Leu Thr Asp Ala Ala Met Thr Val Gln Lys Asn Ile Glu Ser
385                 390                 395                 400

Arg Ile Gly Val Ser Gly Lys Thr Asp Trp Leu Lys Gln Asp Met Asn
                405                 410                 415

Lys Leu Ile Asp Ser Gln Ala Asn Trp Asn Ile Asp Ser Glu Ser Lys
            420                 425                 430

Gly Asn Asp His Leu Gln Gly Gly Ala Leu Leu Tyr Val Asn Asp Asp
        435                 440                 445

Lys Thr Pro Asn Ala Asn Ser Asp Tyr Arg Leu Leu Asn Arg Thr Pro
450                 455                 460

Thr Asn Gln Thr Gly Gln Ile Thr Asp Pro Ser Lys Gln Gly Gly Tyr
465                 470                 475                 480

Glu Met Leu Leu Ala Asn Asp Val Asp Asn Ser Asn Pro Val Val Gln
                485                 490                 495

Ala Glu Gln Leu Asn Trp Leu His Tyr Met Met Asn Ile Gly Thr Ile
            500                 505                 510

Ala Gln Asn Asp Pro Thr Ala Asn Phe Asp Gly Tyr Arg Val Asp Ala
        515                 520                 525

Val Asp Asn Val Asp Ala Asp Leu Leu Gln Ile Ala Gly Asp Tyr Phe
530                 535                 540

Lys Ala Ala Tyr Gly Thr Gly Lys Thr Glu Ala Asn Ala Asn Asn His
```

```
                                    -continued
545                  550                  555                  560

Ile Ser Ile Leu Glu Asp Trp Asp Asn Asn Asp Ser Ala Tyr Ile Lys
                565                  570                  575

Ala His Gly Asn Asn Gln Leu Thr Met Asp Phe Pro Ala His Leu Ala
                580                  585                  590

Leu Lys Tyr Ala Leu Asn Met Pro Leu Ala Ala Gln Ser Gly Leu Glu
                595                  600                  605

Pro Leu Ile Asn Thr Ser Leu Val Lys Arg Gly Lys Asp Ala Thr Glu
                610                  615                  620

Asn Glu Ala Gln Pro Asn Tyr Ala Phe Ile Arg Ala His Asp Ser Glu
625                  630                  635                  640

Val Gln Thr Val Ile Ala Gln Ile Ile Lys Asp Lys Ile Asn Thr Lys
                645                  650                  655

Ser Asp Gly Leu Thr Val Thr Pro Asp Glu Ile Lys Gln Ala Phe Thr
                660                  665                  670

Ile Tyr Asn Ala Asp Glu Leu Lys Ala Asp Lys Glu Tyr Thr Ala Tyr
                675                  680                  685

Asn Ile Pro Ala Ser Tyr Ala Val Leu Leu Thr Asn Lys Asp Thr Val
                690                  695                  700

Pro Arg Val Tyr Tyr Gly Asp Leu Phe Ser Asp Asp Gly Gln Tyr Met
705                  710                  715                  720

Ser Gln Lys Ser Pro Tyr Tyr Asp Ala Ile Thr Ser Leu Leu Lys Ser
                725                  730                  735

Arg Ile Lys Tyr Val Ala Gly Gly Gln Ser Met Asn Met Thr Tyr Leu
                740                  745                  750

His Glu Cys Phe Asp Pro Ala Lys Asn Glu Thr Lys Pro Gln Gly Val
                755                  760                  765

Leu Thr Ser Val Arg Tyr Gly Lys Gly Ala Met Thr Ala Asp Asp Leu
                770                  775                  780

Gly Asn Ser Asp Thr Arg Gln Gln Gly Ile Gly Leu Val Ile Asn Asn
785                  790                  795                  800

Lys Pro Phe Leu Asn Leu Asn Asp Asp Glu Gln Ile Val Leu Asn Met
                805                  810                  815

Gly Ala Ala His Lys Asn Gln Ala Tyr Arg Pro Leu Met Leu Thr Thr
                820                  825                  830

Lys Ser Gly Leu Gln Ile Tyr Asp Lys Asp Ala Gly Ala Pro Val Val
                835                  840                  845

Tyr Thr Asn Asp Ala Gly Gln Leu Ile Phe Lys Ser Asp Met Val Tyr
                850                  855                  860

Gly Val Ser Asn Pro Gln Val Ser Gly Tyr Phe Ala Ala Trp Val Pro
865                  870                  875                  880

Val Gly Ala Ser Asp Ser Gln Asp Ala Arg Thr Gln Ser Ser Gln Ser
                885                  890                  895

Glu Thr Lys Asp Gly Asp Val Tyr His Ser Asn Ala Ala Leu Asp Ser
                900                  905                  910

Asn Val Ile Tyr Glu Gly Phe Ser Asn Phe Gln Ala Met Pro Glu Lys
                915                  920                  925

Asn Asp Asp Phe Thr Asn Val Lys Ile Ala Gln Asn Ala Lys Leu Phe
                930                  935                  940

Lys Asp Leu Gly Ile Thr Ser Phe Glu Leu Ala Pro Gln Tyr Arg Ser
945                  950                  955                  960

Ser Thr Asp Asn Ser Phe Leu Asp Ser Val Ile Gln Asn Gly Tyr Ala
                965                  970                  975
```

```
Phe Thr Asp Arg Tyr Asp Val Gly Tyr Asn Thr Pro Thr Lys Tyr Gly
            980                 985                 990

Thr Val Asp Gln Leu Leu Asp Ser Leu Arg Ala Leu His Ala Gln Gly
            995                1000                1005

Ile Gln Ala Ile Asn Asp Trp Val Pro Asp Gln Ile Tyr Asn Leu Pro
   1010                1015                1020

Gly Glu Gln Ile Val Thr Ala Val Arg Thr Asn Gly Ser Gly Lys Tyr
1025                1030                1035                1040

Asp Tyr Asp Ser Val Ile Asn Asn Thr Leu Tyr Asp Ser Arg Thr Val
            1045                1050                1055

Gly Gly Gly Glu Tyr Gln Glu Lys Phe Gly Gly Leu Phe Leu Asp Gln
            1060                1065                1070

Leu Lys Lys Asp Tyr Pro Ser Leu Phe Glu Thr Lys Gln Ile Ser Thr
            1075                1080                1085

Asn Gln Pro Met Asn Pro Asp Val Lys Ile Lys Glu Trp Ser Ala Lys
            1090                1095                1100

Tyr Phe Asn Gly Ser Asn Ile Gln Gly Arg Gly Ala Trp Tyr Val Leu
1105                1110                1115                1120

Lys Asp Trp Ala Thr Asn Gln Tyr Phe Asn Val Ser Ser Asp Asn Gly
            1125                1130                1135

Phe Leu Pro Lys Gln Leu Leu Gly Glu Lys Thr Ser Thr Gly Phe Ile
            1140                1145                1150

Thr Glu Asn Gly Lys Thr Ser Phe Tyr Ser Thr Ser Gly Tyr Gln Ala
            1155                1160                1165

Lys Asp Thr Phe Ile Gln Asp Gly Thr Asn Trp Tyr Tyr Phe Asp Asn
   1170                1175                1180

Ala Gly Tyr Met Leu Thr Gly Lys Gln Asn Ile His Asp Lys Asn Tyr
1185                1190                1195                1200

Tyr Phe Leu Pro Asn Gly Val Glu Leu Gln Asp Ala Tyr Leu Phe Asp
            1205                1210                1215

Gly Asn Gln Glu Phe Tyr Tyr Asn Lys Ala Gly Glu Gln Val Met Asn
            1220                1225                1230

Gln Tyr Tyr Gln Asp Ser Gln Asn Gln Trp His Tyr Phe Phe Glu Asn
            1235                1240                1245

Gly Arg Met Ala Ile Gly Leu Thr Glu Val Pro Asn Ala Asp Gly Thr
   1250                1255                1260

His Val Thr Gln Tyr Phe Asp Ala Asn Gly Val Gln Ile Lys Gly Thr
1265                1270                1275                1280

Ala Ile Lys Asp Gln Asn Asn Gln Leu Arg Tyr Phe Asp Glu Ala Thr
            1285                1290                1295

Gly Asn Met Val Val Asn Ser Trp Gly Gln Leu Ala Asp Lys Ser Trp
            1300                1305                1310

Leu Tyr Leu Asn Ala Gln Gly Val Ala Val Thr Gly Asn Gln Lys Ile
            1315                1320                1325

Asp Gly Glu Glu Tyr Tyr Phe Asn Ala Asp Gly Lys Gln Val Lys Gly
            1330                1335                1340

Asn Ala Ile Ile Asp Asn Asn Gly Asp Gln Arg Tyr Tyr Asp Gly Asp
1345                1350                1355                1360

Lys Gly Val Met Val Val Asn Ser Trp Gly Glu Leu Pro Asp Gly Ser
            1365                1370                1375

Trp Leu Tyr Leu Asn Asp Lys Gly Ile Ala Val Thr Gly Arg Gln Val
            1380                1385                1390
```

```
Ile Asn Asn Gln Val Asn Phe Phe Gly Asn Asp Gly Lys Gln Ile Lys
         1395                1400                1405

Asp Ala Phe Lys Leu Leu Ser Asp Gly Ser Trp Val Tyr Leu Asp Asp
    1410                1415                1420

Lys Gly Leu Ile Thr Thr Gly Ala Lys Val Ile Asn Gly Leu Asn Met
1425                1430                1435                1440

Phe Phe Asp Lys Asp Gly His Gln Ile Lys Gly Asp Ala Ser Thr Asp
             1445                1450                1455

Ala Asn Gly Lys Arg His Tyr Tyr Asp Lys Asn Asp Gly His Leu Val
         1460                1465                1470

Thr Asn Ser Trp Gly Glu Leu Pro Asp Gly Ser Trp Leu Tyr Leu Glu
    1475                1480                1485

Glu Gln Gly Asp Ala Val Thr Gly Gln Arg Val Ile Asp Gly Lys Thr
1490                1495                1500

Arg Tyr Phe Asp Glu Asp Gly Lys Gln Ile Lys Asn Ser Leu Lys Thr
1505                1510                1515                1520

Leu Ala Asn Gly Asp Lys Ile Tyr Leu Asp Gly Asp Gly Val Ala Ala
             1525                1530                1535

Thr Gly Leu Gln His Val Gly Asp Lys Ile Met Tyr Phe Asp Glu Asp
         1540                1545                1550

Gly Lys Gln Val Val Gly Lys Phe Val Ser Ala Lys Asp Gly Ser Trp
    1555                1560                1565

Tyr Tyr Leu Asn Gln Asp Gly Val Ala Ala Val Gly Pro Ser Ser Ile
    1570                1575                1580

Asn Gly Gln Ser Leu Tyr Phe Asp Gln Asp Gly Lys Gln Val Lys Tyr
1585                1590                1595                1600

Asn Glu Val Arg Asn Ser Asp Gly Thr Thr Asn Tyr Tyr Thr Gly Leu
             1605                1610                1615

Thr Gly Glu Lys Leu Thr Gln Asp Phe Gly Glu Leu Pro Asp Gly Ser
         1620                1625                1630

Trp Ile Tyr Leu Asp Ala Gln Gly His Thr Val Thr Gly Ala Gln Ile
    1635                1640                1645

Ile Asn Gly Gln Asn Leu Tyr Phe Lys Ala Asp Gly Gln Gln Val Lys
    1650                1655                1660

Gly His Ala Tyr Thr Asp Gln Leu Gly His Met Arg Phe Tyr Asp Pro
1665                1670                1675                1680

Asp Ser Gly Asp Met Leu Ser Asn Arg Phe Glu Gln Ile Thr Pro Gly
             1685                1690                1695

Val Trp Ala Tyr Phe Gly Ala Asp Gly Val Ala Ile Thr Gly Gln His
         1700                1705                1710

Asp Ile Asn Gly Gln Lys Leu Phe Phe Asp Glu Thr Gly Tyr Gln Val
    1715                1720                1725

Lys Gly Ser Gln Arg Thr Ile Asp Gly Thr Leu Tyr Ser Phe Asp Ser
    1730                1735                1740

Gln Thr Gly Asn Gln Lys Arg Val Gln Thr Thr Leu Leu Pro Gln Ala
1745                1750                1755                1760

Gly His Tyr Ile Thr Lys Asn Gly Asn Asp Trp Gln Tyr Asp Thr Asn
             1765                1770                1775

Gly Glu Leu Ala Lys Gly Leu Arg Gln Asp Ser Asn Gly Lys Leu Arg
         1780                1785                1790

Tyr Phe Asp Leu Thr Thr Gly Ile Gln Ala Lys Gly Gln Phe Val Thr
    1795                1800                1805

Ile Gly Gln Glu Thr Tyr Tyr Phe Ser Lys Asp His Gly Asp Ala Gln
```

-continued

```
                1810                1815                1820
Leu Leu Pro Met Val Thr Glu Gly His Tyr Gly Thr Ile Thr Leu Lys
1825                1830                1835                1840

Gln Gly Gln Asp Thr Lys Thr Ala Trp Val Tyr Arg Asp Gln Asn Asn
                1845                1850                1855

Thr Ile Leu Lys Gly Leu Gln Asn Ile Asn Gly Thr Leu Gln Phe Phe
                1860                1865                1870

Asp Pro Tyr Thr Gly Glu Gln Leu Lys Gly Gly Val Ala Lys Tyr Asp
                1875                1880                1885

Asp Lys Leu Phe Tyr Phe Glu Ser Gly Lys Gly Asn Leu Val Ser Thr
                1890                1895                1900

Val Ala Gly Asp Tyr Gln Asp Gly His Tyr Ile Ser Gln Asp Gly Gln
1905                1910                1915                1920

Thr Arg Tyr Ala Asp Lys Gln Asn Gln Leu Val Lys Gly Leu Val Thr
                1925                1930                1935

Val Asn Gly Ala Leu Gln Tyr Phe Asp Asn Ala Thr Gly Asn Gln Ile
                1940                1945                1950

Lys Asn Gln Gln Val Ile Val Asp Gly Lys Thr Tyr Tyr Phe Asp Asp
                1955                1960                1965

Lys Gly Asn Gly Glu Tyr Leu Phe Thr Asn Thr Leu Asp Met Ser Thr
                1970                1975                1980

Asn Ala Phe Ser Thr Lys Asn Val Ala Phe Asn His Asp Ser Ser Ser
1985                1990                1995                2000

Phe Asp His Thr Val Asp Gly Phe Leu Thr Ala Asp Thr Trp Tyr Arg
                2005                2010                2015

Pro Lys Ser Ile Leu Ala Asn Gly Thr Thr Trp Arg Asp Ser Thr Asp
                2020                2025                2030

Lys Asp Met Arg Pro Leu Ile Thr Val Trp Trp Pro Asn Lys Asn Val
                2035                2040                2045

Gln Val Asn Tyr Leu Asn Phe Met Lys Ala Asn Gly Leu Leu Thr Thr
                2050                2055                2060

Ala Ala Gln Tyr Thr Leu His Ser Asp Gln Tyr Asp Leu Asn Gln Ala
2065                2070                2075                2080

Ala Gln Asp Val Gln Val Ala Ile Glu Arg Arg Ile Ala Ser Glu His
                2085                2090                2095

Gly Thr Asp Trp Leu Gln Lys Leu Leu Phe Glu Ser Gln Asn Asn Asn
                2100                2105                2110

Pro Ser Phe Val Lys Gln Gln Phe Ile Trp Asn Lys Asp Ser Glu Tyr
                2115                2120                2125

His Gly Gly Gly Asp Ala Trp Phe Gln Gly Gly Tyr Leu Lys Tyr Gly
                2130                2135                2140

Asn Asn Pro Leu Thr Pro Thr Thr Asn Ser Asp Tyr Arg Gln Pro Gly
2145                2150                2155                2160

Asn Ala Phe Asp Phe Leu Leu Ala Asn Asp Val Asp Asn Ser Asn Pro
                2165                2170                2175

Val Val Gln Ala Glu Asn Leu Asn Trp Leu His Tyr Leu Met Asn Phe
                2180                2185                2190

Gly Thr Ile Thr Ala Gly Gln Asp Asp Ala Asn Phe Asp Ser Ile Arg
                2195                2200                2205

Ile Asp Ala Val Asp Phe Ile His Asn Asp Thr Ile Gln Arg Thr Tyr
                2210                2215                2220

Asp Tyr Leu Arg Asp Ala Tyr Gln Val Gln Gln Ser Glu Ala Lys Ala
2225                2230                2235                2240
```

-continued

```
Asn Gln His Ile Ser Leu Val Glu Ala Gly Leu Asp Ala Gly Thr Ser
            2245                2250                2255

Thr Ile His Asn Asp Ala Leu Ile Glu Ser Asn Leu Arg Glu Ala Ala
            2260                2265                2270

Thr Leu Ser Leu Thr Asn Glu Pro Gly Lys Asn Lys Pro Leu Thr Asn
            2275                2280                2285

Met Leu Gln Asp Val Asp Gly Gly Thr Leu Ile Thr Asp His Thr Gln
            2290                2295                2300

Asn Ser Thr Glu Asn Gln Ala Thr Pro Asn Tyr Ser Ile Ile His Ala
2305                2310                2315                2320

His Asp Lys Gly Val Gln Glu Lys Val Gly Ala Ala Ile Thr Asp Ala
            2325                2330                2335

Thr Gly Ala Asp Trp Thr Asn Phe Thr Asp Glu Gln Leu Lys Ala Gly
            2340                2345                2350

Leu Glu Leu Phe Tyr Lys Asp Gln Arg Ala Thr Asn Lys Lys Tyr Asn
            2355                2360                2365

Ser Tyr Asn Ile Pro Ser Ile Tyr Ala Leu Met Leu Thr Asn Lys Asp
            2370                2375                2380

Thr Val Pro Arg Met Tyr Tyr Gly Asp Met Tyr Gln Asp Asp Gly Gln
2385                2390                2395                2400

Tyr Met Ala Asn Lys Ser Ile Tyr Tyr Asp Ala Leu Val Ser Leu Met
            2405                2410                2415

Thr Ala Arg Lys Ser Tyr Val Ser Gly Gly Gln Thr Met Ser Val Asp
            2420                2425                2430

Asn His Gly Leu Leu Lys Ser Val Arg Phe Gly Lys Asp Ala Met Thr
            2435                2440                2445

Ala Asn Asp Leu Gly Thr Ser Ala Thr Arg Thr Glu Gly Leu Gly Val
            2450                2455                2460

Ile Ile Gly Asn Asp Pro Lys Leu Gln Leu Asn Asp Ser Asp Lys Val
2465                2470                2475                2480

Thr Leu Asp Met Gly Ala Ala His Lys Asn Gln Lys Tyr Arg Ala Val
            2485                2490                2495

Ile Leu Thr Thr Arg Asp Gly Leu Ala Thr Phe Asn Ser Asp Gln Ala
            2500                2505                2510

Pro Thr Ala Trp Thr Asn Asp Gln Gly Thr Leu Thr Phe Ser Asn Gln
            2515                2520                2525

Glu Ile Asn Gly Gln Asp Asn Thr Gln Ile Arg Gly Val Ala Asn Pro
            2530                2535                2540

Gln Val Ser Gly Tyr Leu Ala Val Trp Val Pro Val Gly Ala Ser Asp
2545                2550                2555                2560

Asn Gln Asp Ala Arg Thr Ala Ala Thr Thr Thr Glu Asn His Asp Gly
            2565                2570                2575

Lys Val Leu His Ser Asn Ala Ala Leu Asp Ser Asn Leu Ile Tyr Glu
            2580                2585                2590

Gly Phe Ser Asn Phe Gln Pro Lys Ala Thr Thr His Asp Glu Leu Thr
            2595                2600                2605

Asn Val Val Ile Ala Lys Asn Ala Asp Val Phe Asn Asn Trp Gly Ile
            2610                2615                2620

Thr Ser Phe Glu Met Ala Pro Gln Tyr Arg Ser Ser Gly Asp His Thr
2625                2630                2635                2640

Phe Leu Asp Ser Thr Ile Asp Asn Gly Tyr Ala Phe Thr Asp Arg Tyr
            2645                2650                2655
```

-continued

Asp Leu Gly Phe Asn Thr Pro Thr Lys Tyr Gly Thr Asp Gly Asp Leu
         2660                2665                2670

Arg Ala Thr Ile Gln Ala Leu His His Ala Asn Met Gln Val Met Ala
         2675                2680                2685

Asp Val Val Asp Asn Gln Val Tyr Asn Leu Pro Gly Lys Glu Val Val
         2690                2695                2700

Ser Ala Thr Arg Ala Gly Val Tyr Gly Asn Asp Asp Ala Thr Gly Phe
2705                 2710                2715                2720

Gly Thr Gln Leu Tyr Val Thr Asn Ser Val Gly Gly Gln Tyr Gln
         2725                2730                2735

Glu Lys Tyr Ala Gly Gln Tyr Leu Glu Ala Leu Lys Ala Lys Tyr Pro
         2740                2745                2750

Asp Leu Phe Glu Gly Lys Ala Tyr Asp Tyr Trp Tyr Lys Asn Tyr Ala
         2755                2760                2765

Asn Asp Gly Ser Asn Pro Tyr Tyr Thr Leu Ser His Gly Asp Arg Glu
         2770                2775                2780

Ser Ile Pro Ala Asp Val Ala Ile Lys Gln Trp Ser Ala Lys Tyr Met
2785                 2790                2795                2800

Asn Gly Thr Asn Val Leu Gly Asn Gly Met Gly Tyr Val Leu Lys Asp
         2805                2810                2815

Trp His Asn Gly Gln Tyr Phe Lys Leu Asp Gly Asp Lys Ser Thr Leu
         2820                2825                2830

Pro Gln Ile
     2835

<210> SEQ ID NO 3
<211> LENGTH: 2568
<212> TYPE: DNA
<213> ORGANISM: Leuconostoc mesenteroides
<220> FEATURE:
<223> OTHER INFORMATION: catalytic domain

<400> SEQUENCE: 3
gatatgtcta ctaatgcttt ttctaccaaa aatgttgcat tcaatcatga cagtagcagt      60
ttcgaccata ctgttgatgg cttcttgacg gcagatactt ggtatcgacc aaagtcaatt     120
ttggctaacg ggacaacttg gcgtgattcg actgataagg atatgcgacc attaatcact     180
gtttggtggc aaataagaa tgttcaagtc aactacctca acttcatgaa agcaaatggc     240
ttgttgacaa cagcagcaca atacacacta cattcagatc aatatgattt gaaccaagct     300
gcacaagatg ttcaagtggc cattgaaagg cgcattgcgt cagagcatgg cacagactgg     360
ttacagaaat tgttgtttga atcacaaaat aataacccat catttgtgaa gcaacaattc     420
atttggaaca aggattctga atatcatggt ggtggtgatg cttggttcca agtggttat     480 ctgaagtatg caataaccc actcacacca caactaatt ctgattatcg tcaacctggt     540
aatgcatttg atttcttgct agccaacgac gtggataatt ctaatcctgt tgtgcaagct     600
gaaaacttaa actggttaca ttacttaatg aactttggca ccatcactgc gggtcaagat     660
gacgctaatt ttgatagtat tcgtattgac gctgtcgact ttattcataa tgatacaatc     720
caacgtactt atgattatct tcgtgatgct tatcaagtgc aacaaagtga agccaaagca     780
aaccagcaca tttcattggt tgaagctggc ttagacgcag gtacatcaac gattcataat     840
gatgcgttaa ttgagtcaaa cctccgtgaa gcagcgacat tgtcgttaac aaatgaacct     900
ggtaaaaata aaccattgac gaatatgcta caagacgttg acggcggtac gcttatcacc     960
gaccatacgc agaatagtac agaaaatcag gcgacaccaa actattcaat tattcacgcg    1020

```
cacgataaag gtgtgcaaga aaaagtaggt gcagccatta ctgatgctac tggtgctgat    1080
tggacgaact ttacagatga acagttaaaa gccggattag agctattcta taaggatcag    1140
cgcgcaacaa acaaaaagta taatagttat aacataccaa gtatttatgc cctgatgttg    1200
acaaacaaag atactgttcc tcgtatgtat tatggggata tgtatcaaga tgacggacag    1260
tatatggcaa acaagagtat ctactatgat gccttagtgt cattaatgac ggctcgtaaa    1320
agctatgtca gcggtggtca aactatgagt gttgacaatc atggtttgtt gaagagtgtc    1380
cgttttggaa aagatgcgat gacagctaat gatttaggta catcagctac gcgtactgag    1440
ggtcttggtg tcattattgg taatgatcca agttgcaac ttaatgattc ggataaagtg     1500
acactggata tgggtgcagc acataaaaat caaaagtatc gcgcagttat cttaacaaca    1560
cgtgatggtt tggcaacctt taattcagat caagcaccaa cagcttggac aaacgatcaa    1620
ggaacgttaa cattctcaaa tcaagagatt aacgggcaag acaatacaca aattcgtggt    1680
gttgctaatc cgcaagtttc tggttatcta gctgtttggg tgcctgtggg tgcatcagac    1740
aatcaagatg cccgtacagc agcaacgaca acagaaaatc atgatggtaa agtattacac    1800
tcgaatgcgg cattagattc taaccttatt tatgaaggtt tctctaactt ccaacctaag    1860
gcaacaacgc atgatgaact tacgaacgtt gtaattgcta aaaatgccga tgtcttcaat    1920
aattggggta ttacgagttt tgaaatggca ccacagtacc gttcaagtgg ggaccataca    1980
ttcttggatt caacgattga taatggttat gccttcactg atcgctatga cttaggtttc    2040
aatacaccaa caaagtatgg cactgatggt gatttgcgtg caacgattca agcgctacat    2100
catgctaata tgcaagttat ggctgacgtt gttgataacc aggtctataa cttacctggt    2160
aaagaagttg tttcagcaac acgagcaggt gtttatggta atgacgacgc cacgggcttt    2220
ggaacgcaac tctatgtgac taactccgtt ggtggtggtc aataccaaga gaaatatgct    2280
ggacaatact tagaagctct gaaagcaaag tatccagacc tctttgaggg taaggcctat    2340
gattattggt ataagaacta tgcaaatgat gggtcaaatc cttactatac attgtcacac    2400
ggtgaccgtg aatctatccc agcagatgtt gctattaagc aatggtcagc taagtatatg    2460
aacggcacga acgttttggg caatggtatg ggttatgtat tgaaggattg gcataatggt    2520
caatatttca gcttgatgg tgataaatca acattacctc aaatttaa                  2568
```

```
<210> SEQ ID NO 4
<211> LENGTH: 8506
<212> TYPE: DNA
<213> ORGANISM: Leuconostoc mesenteroides
<220> FEATURE:
<223> OTHER INFORMATION: Coding sequence DSR-E

<400> SEQUENCE: 4
```

```
atgagagaca tgagggtaat ttgtgaccgt aaaaaattgt acaaatcggg caaagtacta     60
gtaacagccg gtattttgc tttgatgatg tttggcgtca caactgctag tgttagtgca    120
aatacgattg cagttgacac gaatcatagc cgtacttcag cacagattaa taagagtgcc    180
gttgataagg ttaatgatga caagactact ttaggagcgg caaaagtagt ggcagtagcc    240
acaacgccag cgacaccggt agcagataaa acagtaagtg cacccgcagc agataaggca    300
gtagatacaa cgtcatcaac gacacctgca acggataagg cagtagatac aacgccaacg    360
acacctgcag cagataaggc agtagataca acgccaacga cacctgcagc agataaggca    420
gtagatacaa cgccaacgac acctgcagca aataaagcag tagatacaac gccagcgacc    480
```

-continued

```
gctgcaacag ataaggcggt agccacgcca gccacacctg cagcagataa gctagcaaat    540
acgacgcctg caacggacaa ggcagtagcc acaacgccag cgacgccggt agcaaataaa    600
gcagcagaca cgagtagtat tcatgatcaa ccattagata caaatgtgcc aactgataaa    660
tcagcaaacc tcgtctcgac aacacaaaaa agtacggata atcaacaagt taagtctaca    720
gaaacatctc atcttcaaga aatcaacggt aaaacctatt ttcttgacga caatggtcaa    780
gttaaaaaga acttcaccgc tattattgac ggtaaagttc tatactttga taaaacatcc    840
ggcgaattga ccgcaaatgc accgcaagtt actaagggat tagtaaatat tgataatgca    900
cataacgcgg ctcatgatct cacagctgat aacttcacaa atgtcgatgg ttacttaaca    960
gctaacagtt ggtatcgtcc taaggacatc ttaaaaaacg gaacgacctg gacaccaaca   1020
acagcagaag atttttcgacc attgctcatg tcttggtggc cggataagaa tacgcaggta   1080
gcttatctac aatatatgca atcagttggt atgctacctg acgatgttaa agtatcaaat   1140
gatgataata tgagcacatt gactgatgct gctatgactg ttcaaaagaa tatcgaatcg   1200
cgaattggtg tatctggaaa aactgattgg ctcaagcaag atatgaacaa actgattgat   1260
tcacaggcaa attggaatat tgatagtgaa tcaaagggta atgatcattt acagggtggg   1320
gcattgttat atgtgaatga tgacaaaaca cctaacgcga actcagatta ccgtctgtta   1380
aaccgtacac caaccaacca aaccggccaa attactgatc caagtaaaca aggtggatat   1440
gagatgttat tagctaatga tgttgataat tctaaccctg ttgtacaagc tgagcaattg   1500
aactggcttc actacatgat gaacattggt actatagctc agaacgaccc aacagctaat   1560
tttgacggtt atcgtgttga tgcggttgat aacgttgatg ccgatctctt acaaattgct   1620
ggtgattact ttaaagctgc atacggtact ggtaaaactg aggcaaacgc aaacaatcat   1680
atttcgatct tggaagattg ggataataat gattctgcgt acattaaagc ccacgggaat   1740
aaccaattga caatggattt tccagcacac ttggctttga atacgccttt gaacatgcct   1800
cttgccgcac aaagtggcct agaaccgcta attaatacaa gtcttgttaa gcgtgggaaa   1860
gatgccacag aaaatgaagc acaaccaaac tatgccttta tccgtgccca tgatagtgaa   1920
gtgcagaccg ttattgcaca aattattaag gataaaatta acacaaaatc agacggctta   1980
actgtaacac cagatgagat taagcaagct ttcactattt acaacgccga tgaattaaaa   2040
gcagataagg aatatacagc atacaatatt cctgcttctt acgctgtatt gttgacaaac   2100
aaggatactg tgccacgtgt ttattatggt gatctatttt ctgatgatgg acagtatatg   2160
tcacagaagt caccatacta tgacgccatt acgtcacttt tgaaaagccg tatcaaatat   2220
gttgctggtg gtcaaagtat gaatatgacg tacttgcatg agtgctttga tccagcaaaa   2280
aatgagacaa agccacaagg tgtcttaaca tcagtacgtt acggtaaagg tgcgatgacg   2340
gctgacgatt tgggtaatag tgacacacgt caacaaggta ttggtttggt gattaataat   2400
aagccattct tgaatttaaa tgatgatgaa caaattgtgc tcaatatggg tgctgctcac   2460
aaaaatcaag cttaccgacc acttatgttg acaacaaaat ctggtcttca aatttacgat   2520
aaggatgccg gagcgccagt tgtttatact aacgatgctg gtcaacttat ttttaagtca   2580
gatatggtct atggtgtcag caatccacag gtatctggtt attttgctgc atgggtacca   2640
gtcggtgcga gtgatagtca agatgctaga acacaaagca gccagtcaga aactaaggat   2700
ggcgatgtct atcattcaaa tgctgcgctt gattctaatg tgatttatga aggcttctcg   2760
aatttccaag caatgcctga aaagaatgat gacttcacca acgtaaaaat tgctcaaaat   2820
gctaaattgt ttaaagattt agggattaca agctttgaat tagcaccgca atatcgttca   2880
```

-continued

```
agtacagata atagttttt  ggattcggtt  atccaaaacg  gctatgcctt  tactgatcga   2940
tatgatgttg  gctataatac  gccaacaaaa  tatggtacag  ttgatcaact  tctagatagt   3000
ctaagagcat  tacacgcaca  aggtattcag  gctattaatg  actgggtacc  tgatcaaatt   3060
tataatttac  ctggcgaaca  aatcgtcacc  gcagttcgta  caaatggttc  aggtaagtac   3120
gattatgatt  cagtgattaa  taacacgctc  tatgattcac  gaacagttgg  gggcggcgaa   3180
taccaagaaa  agtttggtgg  cctgttctta  gaccagttga  aaaaagatta  tcctagcttg   3240
tttgaaacta  agcagatatc  aacgaatcag  ccgatgaatc  cggatgttaa  aattaaagaa   3300
tggtctgcaa  agtactttaa  tggttcaaac  attcaaggtc  gtggcgcttg  gtatgtactt   3360
aaagactggg  caacaaatca  atatttcaat  gtgtctagtg  ataatggatt  cttgcctaaa   3420
cagttactgg  gtgaaaaaac  aagcaccggc  tttataacag  aaaatggtaa  gacttctttc   3480
tactcaacaa  gtggttatca  agctaaagat  acctttattc  aagatggaac  aaattggtat   3540
tactttgata  atgcaggcta  tatgttgaca  ggtaaacaaa  atatccacga  taaaaattat   3600
tatttcttac  ctaatggtgt  ggaacttcaa  gatgcttacc  ttttgatgg  taatcaagaa   3660 ttttactata  ataaagctgg  ggaacaagtt  atgaaccagt  attatcaaga  tagtcaaaat   3720
caatggcatt  atttctttga  aaatggtcgc  atggcaattg  gcctgacaga  agttccgaac   3780
gctgatggca  cccatgttac  acaatatttt  gatgctaatg  gtgtccaaat  taaaggcaca   3840
gctataaaag  atcagaataa  tcaattacgc  tattttgatg  aggccacagg  taatatggtg   3900
gttaattcat  ggggacagtt  agcagataag  tcttggcttt  accttaatgc  acaaggcgtt   3960
gctgtgactg  gtaaccaaaa  aattgatggt  gaagagtact  acttcaatgc  tgatggtaag   4020
caagttaaag  gcaatgcaat  catcgataat  aatggtgatc  aacgttatta  tgatggtgat   4080
aagggtgtca  tggtagttaa  ttcatggggt  gagttgccag  atggctcatg  gttatatttg   4140
aatgacaaag  gtattgctgt  aacaggccgt  caagtcatta  ataatcaagt  taatttcttt   4200
ggtaatgatg  gtaagcaaat  caaagatgcc  tttaaattat  tatccgatgg  ttcatgggtg   4260
tatttggatg  ataagggcct  gataacaact  ggagccaaag  ttatcaatgg  tctaaatatg   4320
ttttttgata  aagacggtca  tcaaatcaaa  ggtgatgcca  gcacggatgc  caatggtaag   4380
cgccattatt  atgacaaaaa  tgatggtcat  cttgtcacaa  attcatgggg  tgagttgcca   4440
gatggttcat  ggttatatct  agaagaacaa  ggtgatgctg  ttactggtca  acgtgtgatt   4500
gatggcaaga  cacgctattt  tgatgaagat  ggcaaacaaa  ttaaaaatag  cctaaaaacg   4560
ctggccaatg  gcgataagat  ttatcttgat  ggtgatgggg  ttgctgcaac  aggcttacaa   4620
catgtgggcg  ataaaatcat  gtattttgat  gaagatggca  acaagttgt  tggcaagttt   4680 gtatcagcaa  aagatggttc  atggtattac  ttaaatcagg  atggtgttgc  cgcggttggt   4740
ccaagcagca  ttaatggaca  atcactttac  tttgatcaag  atggtaaaca  agttaaatat   4800
aatgaagttc  gtaatagtga  tggaacaacc  aactattaca  caggattaac  gggtgaaaag   4860
ttaacgcaag  acttcggtga  actaccagat  ggttcatgga  tttatcttga  tgcgcaaggt   4920
catacagtaa  ctggtgcaca  aatcattaac  ggtcaaaatc  tttactttaa  ggctgacggc   4980
cagcaagtta  aggtcatgc   ttatactgac  caattaggtc  atatgcgttt  ttatgatcct   5040
gattcaggtg  atatgttgag  taatcgcttt  gaacaaatca  cacctggtgt  atgggcttac   5100
tttggtgctg  atggtgtggc  cataactgga  caacatgaca  taaatggtca  gaagctattc   5160
tttgatgaga  caggatatca  agttaaaggt  tcgcaacgta  caatagatgg  tacgttatac   5220
```

```
agcttcgatt ctcaaactgg taaccaaaaa cgcgtacaga caacattgtt gccacaagca    5280
ggtcactata tcacgaaaaa tggtaacgat tggcagtatg ataccaatgg tgaactagcg    5340
aagggtctgc gtcaagatag caatggtaag ttgcgttact ttgatttgac aaccggcata    5400
caagcgaaag gccaatttgt tacaattggc caagaaactt attactttag taaagatcac    5460
ggggatgcgc agttattgcc aatggtcact gaagggcatt acgtacaat aacactcaag    5520 caaggtcaag acaccaaaac agcctgggtt taccgtgatc aaaataatac tattttgaag    5580
ggattgcaaa atatcaatgg cacgttgcaa ttctttgatc catatacagg tgaacaactt    5640
aagggtggcg tagcaaagta tgacgacaag ctctttttact ttgaatcagg taaaggtaat    5700
cttgttagca ccgtagcagg tgactatcag gatggtcatt atatttccca agatggccaa    5760
acacgttacg cagataagca aaatcagctt gtaaagggac ttgttactgt taatgggca    5820 ttacaatact ttgataacgc tactggtaac caaataaaaa atcaacaagt tattgttgat    5880
ggcaagacgt actattttga cgataaaggc aatggtgaat acttattcac taatacatta    5940
gatatgtcta ctaatgcttt ttctaccaaa aatgttgcat tcaatcatga cagtagcagt    6000
ttcgaccata ctgttgatgg cttcttgacg gcagatactc ggtatcgacc aaagtcaatt    6060
ttggctaacg ggacaacttg gcgtgattcg actgataagg atatgcgacc attaatcact    6120
gtttggtggc aaataagaa tgttcaagtc aactacctca acttcatgaa agcaaatggc    6180
ttgttgacaa cagcagcaca atacacacta cattcagatc aatatgattt gaaccaagct    6240
gcacaagatg ttcaagtggc cattgaaagg cgcattgcgt cagagcatgg cacagactgg    6300
ttacagaaat tgttgtttga atcacaaaat aataacccat catttgtgaa gcaacaattc    6360
atttggaaca aggattctga atatcatggt ggtggtgatg cttggttcca aggtggttat    6420
ctgaagtatg gcaataaccc actcacacca acaactaatt ctgattatcg tcaacctggt    6480
aatgcatttg atttcttgct agccaacgac gtggataatt ctaatcctgt tgtgcaagct    6540
gaaaacttaa actggttaca ttacttaatg aactttggca ccatcactgc gggtcaagat    6600
gacgctaatt ttgatagtat tcgtattgac gctgtcgact ttattcataa tgatacaatc    6660
caacgtactt atgattatct tcgtgatgct tatcaagtgc aacaaagtga agccaaagca    6720
aaccagcaca tttcattggt tgaagctggc ttagacgcag gtacatcaac gattcataat    6780
gatgcgttaa ttgagtcaaa cctccgtgaa gcagcgacat tgtcgttaac aaatgaacct    6840
ggtaaaaata aaccattgac gaatatgcta caagacgttg acggcggtac gcttatcacc    6900
gaccatacgc agaatagtac agaaaatcag gcgacaccaa actattcaat tattcacgcg    6960
cacgataaag gtgtgcaaga aaaagtaggt gcagccatta ctgatgctac tggtgctgat    7020
tggacgaact ttacagatga acagttaaaa gccggattag agctattcta taaggatcag    7080
cgcgcaacaa acaaaaagta taatagttat aacataccaa gtatttatgc cctgatgttg    7140
acaaacaaag atactgttcc tcgtatgtat tatgggata tgtatcaaga tgacggacag    7200
tatatggcaa acaagagtat ctactatgat gccttagtgt cattaatgac ggctcgtaaa    7260
agctatgtca gcgtggtcaa actatgagt gttgacaatc atggtttgtt gaagagtgtc    7320
cgttttggaa aagatgcgat gacagctaat gatttaggta catcagctac gcgtactgag    7380
ggtcttggtg tcattattgg taatgatcca aagttgcaac ttaatgattc ggataaagtg    7440
acactggata tgggtgcagc acataaaaat caaaagtatc gcgcagttat cttaacaaca    7500
cgtgatggtt tggcaacctt taattcgat caagcaccaa cagcttggac aaacgatcaa    7560
ggaacgttaa cattctcaaa tcaagagatt aacgggcaag acaatacaca aattcgtggt    7620
```

-continued

| | | |
|---|---|---|
| gttgctaatc cgcaagtttc tggttatcta gctgtttggg tgcctgtggg tgcatcagac | 7680 |
| aatcaagatg cccgtacagc agcaacgaca acagaaaatc atgatggtaa agtattacac | 7740 |
| tcgaatgcgg cattagattc taaccttatt tatgaaggtt tctctaactt ccaacctaag | 7800 |
| gcaacaacgc atgatgaact tacgaacgtt gtaattgcta aaaatgccga tgtcttcaat | 7860 |
| aattggggta ttacgagttt tgaaatggca ccacagtacc gttcaagtgg ggaccataca | 7920 |
| ttcttggatt caacgattga taatggttat gccttcactg atcgctatga cttaggtttc | 7980 |
| aatacaccaa caaagtatgg cactgatggt gatttgcgtg caacgattca agcgctacat | 8040 |
| catgctaata tgcaagttat ggctgacgtt gttgataacc aggtctataa cttacctggt | 8100 |
| aaagaagttg tttcagcaac acgagcaggt gtttatggta atgacgacgc cacgggcttt | 8160 |
| ggaacgcaac tctatgtgac taactccgtt ggtggtggtc aataccaaga gaaatatgct | 8220 |
| ggacaatact tagaagctct gaaagcaaag tatccagacc tctttgaggg taaggcctat | 8280 |
| gattattggt ataagaacta tgcaaatgat gggtcaaatc cttactatac attgtcacac | 8340 |
| ggtgaccgtg aatctatccc agcagatgtt gctattaagc aatggtcagc taagtatatg | 8400 |
| aacggcacga acgttttggg caatggtatg ggttatgtat tgaaggattg gcataatggt | 8460 |
| caatatttca gcttgatgg tgataaatca acattacctc aaattt | 8506 |

<210> SEQ ID NO 5
<211> LENGTH: 8931
<212> TYPE: DNA
<213> ORGANISM: Leuconostoc mesenteroides
<220> FEATURE:
<223> OTHER INFORMATION: Gene dsr-E

<400> SEQUENCE: 5

| | | |
|---|---|---|
| aataatctgt ctccattgct ttcaaaataa taatagttaa ttattatcat ggaacaatca | 60 |
| atattttatt tatattcact attgaatatc cttttttgca taaatctcta gagccgattt | 120 |
| tttgggttat acaatgaatt ggtaaaggtt aatcattttt acaaaaccat ggtggttttt | 180 |
| tattttttct aaaattaccg aactagagga agagaaaagg agcaatagtt gtatgagaga | 240 |
| catgagggta atttgtgacc gtaaaaaatt gtacaaatcg ggcaaagtac tagtaacagc | 300 |
| cggtattttt gctttgatga tgtttggcgt cacaactgct agtgttagtg caaatacgat | 360 |
| tgcagttgac acgaatcata gccgtacttc agcacagatt aataagagtg ccgttgataa | 420 |
| ggttaatgat gacaagacta ctttaggagc ggcaaaagta gtggcagtag ccacaacgcc | 480 |
| agcgacaccg gtagcagata aaacagtaag tgcacccgca gcagataagg cagtagatac | 540 |
| aacgtcatca acgacacctg caacggataa ggcagtagat acaacgccaa cgacacctgc | 600 |
| agcagataag gcagtagata caacgccaac gacacctgca gcagataagg cagtagatac | 660 |
| aacgccaacg acacctgcag caaataaagc agtagataca acgccagcga ccgctgcaac | 720 |
| agataaggcg gtagccacgc cagccacacc tgcagcagat aagctagcaa atacgacgcc | 780 |
| tgcaacggac aaggcagtag ccacaacgcc agcgacgccg gtagcaaata agcagcaga | 840 |
| cacgagtagt attcatgatc aaccattaga tacaaatgtg ccaactgata atcagcaaa | 900 |
| cctcgtctcg acaacacaaa aaagtacgga taatcaacaa gttaagtcta cagaaacatc | 960 |
| tcatcttcaa gaaatcaacg gtaaaaccta ttttcttgac gacaatggtc aagttaaaaa | 1020 |
| gaacttcacc gctattattg acggtaaagt tctatacttt gataaaacat ccggcgaatt | 1080 |
| gaccgcaaat gcaccgcaag ttactaaggg attagtaaat attgataatg cacataacgc | 1140 |

```
ggctcatgat ctcacagctg ataacttcac aaatgtcgat ggttacttaa cagctaacag   1200
ttggtatcgt cctaaggaca tcttaaaaaa cggaacgacc tggacaccaa caacagcaga   1260
agattttcga ccattgctca tgtcttggtg gccggataag aatacgcagg tagcttatct   1320
acaatatatg caatcagttg gtatgctacc tgacgatgtt aaagtatcaa atgatgataa   1380
tatgagcaca ttgactgatg ctgctatgac tgttcaaaag aatatcgaat cgcgaattgg   1440
tgtatctgga aaaactgatt ggctcaagca agatatgaac aaactgattg attcacaggc   1500
aaattggaat attgatagtg aatcaaaggg taatgatcat ttacagggtg gggcattgtt   1560
atatgtgaat gatgacaaaa cacctaacgc gaactcagat taccgtctgt aaaccgtac   1620 accaaccaac caaaccggcc aaattactga tccaagtaaa caaggtggat atgagatgtt   1680
attagctaat gatgttgata attctaaccc tgttgtacaa gctgagcaat tgaactggct   1740
tcactacatg atgaacattg gtactatagc tcagaacgac ccaacagcta atttgacgg    1800 ttatcgtgtt gatgcggttg ataacgttga tgccgatctc ttacaaattg ctggtgatta   1860
ctttaaagct gcatacggta ctggtaaaac tgaggcaaac gcaaacaatc atatttcgat   1920
cttggaagat tgggataata atgattctgc gtacattaaa gcccacggga ataaccaatt   1980
gacaatggat tttccagcac acttggcttt gaaatacgcc ttgaacatgc ctcttgccgc   2040
acaaagtggc ctagaaccgc taattaatac aagtcttgtt aagcgtggga agatgccac    2100 agaaaatgaa gcacaaccaa actatgcctt tatccgtgcc catgatagtg aagtgcagac   2160
cgttattgca caaattatta aggataaaat taacacaaaa tcagacggct taactgtaac   2220
accagatgag attaagcaag ctttcactat ttacaacgcc gatgaattaa aagcagataa   2280
ggaatataca gcatacaata ttcctgcttc ttacgctgta ttgttgacaa acaaggatac   2340
tgtgccacgt gtttattatg gtgatctatt ttctgatgat ggacagtata tgtcacagaa   2400
gtcaccatac tatgacgcca ttcgtcact tttgaaaagc cgtatcaaat atgttgctgg     2460
tggtcaaagt atgaatatga cgtacttgca tgagtgcttt gatccagcaa aaaatgagac   2520
aaagccacaa ggtgtcttaa catcagtacg ttacggtaaa ggtgcgatga cggctgacga   2580
tttgggtaat agtgacacac gtcaacaagg tattggtttg gtgattaata ataagccatt   2640
cttgaattta aatgatgatg aacaaattgt gctcaatatg ggtgctgctc acaaaaatca   2700
agcttaccga ccacttatgt tgacaacaaa atctggtctt caaatttacg ataaggatgc   2760
cggagcgcca gttgtttata ctaacgatgc tggtcaactt attttttaagt cagatatggt   2820 ctatggtgtc agcaatccac aggtatctgg ttattttgct gcatgggtac cagtcggtgc   2880
gagtgatagt caagatgcta aaacacaaag cagccagtca gaaactaagg atggcgatgt   2940
ctatcattca aatgctgcgc ttgattctaa tgtgatttat gaaggcttct cgaatttcca   3000
agcaatgcct gaaagaatg atgacttcac caacgtaaaa attgctcaaa atgctaaatt    3060
gtttaaagat ttagggatta caagctttga attagcaccg caatatcgtt caagtacaga   3120
taatagtttt ttggattcgg ttatccaaaa cggctatgcc tttactgatc gatatgatgt   3180
tggctataat acgccaacaa aatatggtac agttgatcaa cttctagata gtctaagagc   3240
attacacgca caaggtattc aggctattaa tgactgggta cctgatcaaa tttataattt   3300
acctggcgaa caaatcgtca ccgcagttcg tacaaatggt tcaggtaagt acgattatga   3360
ttcagtgatt aataacacgc tctatgattc acgaacagtt gggggcggcg aataccaaga   3420
aaagtttggt ggcctgttct tagaccagtt gaaaaaagat tatcctagct tgtttgaaac   3480
taagcagata tcaacgaatc agccgatgaa tccggatgtt aaaattaaag aatggtctgc   3540
```

-continued

```
aaagtacttt aatggttcaa acattcaagg tcgtggcgct tggtatgtac ttaaagactg    3600
ggcaacaaat caatatttca atgtgtctag tgataatgga ttcttgccta aacagttact    3660
gggtgaaaaa acaagcaccg gctttataac agaaaatggt aagacttctt tctactcaac    3720
aagtggttat caagctaaag ataccttat tcaagatgga acaaattggt attactttga    3780
taatgcaggc tatatgttga caggtaaaca aaatatccac gataaaaatt attatttctt    3840
acctaatggt gtggaacttc aagatgctta ccttttgat ggtaatcaag aattttacta    3900
taataaagct ggggaacaag ttatgaacca gtattatcaa gatagtcaaa atcaatggca    3960
ttatttcttt gaaaatggtc gcatggcaat tggcctgaca gaagttccga acgctgatgg    4020
cacccatgtt acacaatatt tgatgctaa tggtgtccaa attaaaggca cagctataaa    4080
agatcagaat aatcaattac gctattttga tgaggccaca ggtaatatgg tggttaattc    4140
atggggacag ttagcagata agtcttggct ttaccttaat gcacaaggcg ttgctgtgac    4200
tggtaaccaa aaaattgatg gtgaagagta ctacttcaat gctgatggta agcaagttaa    4260
aggcaatgca atcatcgata taatggtga tcaacgttat tatgatggtg ataagggtgt    4320
catggtagtt aattcatggg gtgagttgcc agatggctca tggttatatt tgaatgacaa    4380
aggtattgct gtaacaggcc gtcaagtcat taataatcaa gttaattttct ttggtaatga    4440
tggtaagcaa atcaaagatg cctttaaatt attatccgat ggttcatggg tgtatttgga    4500
tgataagggc ctgataacaa ctggagccaa agttatcaat ggtctaaata tgttttttga    4560
taaagacggt catcaaatca aggtgatgc cagcacggat gccaatggta agcgccatta    4620
ttatgacaaa aatgatggtc atcttgtcac aaattcatgg ggtgagttgc cagatggttc    4680
atggttatat ctagaagaac aaggtgatgc tgttactggt caacgtgtga ttgatggcaa    4740
gacacgctat tttgatgaag atggcaaaca aattaaaaat agcctaaaaa cgctggccaa    4800
tggcgataag atttatcttg atggtgatgg ggttgctgca acaggcttac aacatgtggg    4860
cgataaaatc atgtattttg atgaagatgg caaacaagtt gttggcaagt ttgtatcagc    4920
aaaagatggt tcatggtatt acttaaatca ggatggtgtt gccgcggttg gtccaagcag    4980
cattaatgga caatcacttt actttgatca agatggtaaa caagttaaat ataatgaagt    5040
tcgtaatagt gatggaacaa ccaactatta cacaggatta acgggtgaaa agttaacgca    5100
agacttcggt gaactaccag atggttcatg gattatctt gatgcgcaag gtcatacagt    5160
aactggtgca caaatcatta acggtcaaaa tctttacttt aaggctgacg gccagcaagt    5220
taaaggtcat gcttatactg accaattagg tcatatgcgt ttttatgatc ctgattcagg    5280
tgatatgttg agtaatcgct ttgaacaaat cacacctggt gtatgggctt actttggtgc    5340
tgatggtgtg gccataactg gacaacatga cataaatggt cagaagctat tctttgatga    5400
gacaggatat caagttaaag gttcgcaacg tacaatagat ggtacgttat acagcttcga    5460
ttctcaaact ggtaaccaaa aacgcgtaca gacaacattg ttgccacaag caggtcacta    5520
tatcacgaaa aatggtaacg attggcagta tgataccaat ggtgaactag cgaagggtct    5580
gcgtcaagat agcaatggta agttgcgtta ctttgatttg acaaccggca tacaagcgaa    5640
aggccaattt gttacaattg ccaagaaaac ttattacttt agtaaagatc acggggatgc    5700
gcagttattg ccaatggtca ctgaagggca ttacggtaca ataacactca agcaaggtca    5760
agacaccaaa acagcctggg tttaccgtga tcaaaataat actatttga agggattgca    5820
aaatatcaat ggcacgttgc aattcttga tccatataca ggtgaacaac ttaagggtgg    5880
```

```
cgtagcaaag tatgacgaca agctctttta ctttgaatca ggtaaaggta atcttgttag    5940
caccgtagca ggtgactatc aggatggtca ttatatttcc caagatggcc aaacacgtta    6000
cgcagataag caaaatcagc ttgtaaaggg acttgttact gttaatgggg cattacaata    6060
ctttgataac gctactggta accaaataaa aaatcaacaa gttattgttg atggcaagac    6120
gtactatttt gacgataaag gcaatggtga atacttattc actaatacat tagatatgtc    6180
tactaatgct ttttctacca aaaatgttgc attcaatcat gacagtagca gtttcgacca    6240
tactgttgat ggcttcttga cggcagatac ttggtatcga ccaaagtcaa ttttggctaa    6300
cgggacaact tggcgtgatt cgactgataa ggatatgcga ccattaatca ctgtttggtg    6360
gccaaataag aatgttcaag tcaactacct caacttcatg aaagcaaatg cttgttgac     6420 aacagcagca caatacacac tacattcaga tcaatatgat ttgaaccaag ctgcacaaga    6480
tgttcaagtg gccattgaaa ggcgcattgc gtcagagcat ggcacagact ggttacagaa    6540
attgttgttt gaatcacaaa ataataaccc atcatttgtg aagcaacaat tcatttggaa    6600
caaggattct gaatatcatg gtggtggtga tgcttggttc caaggtggtt atctgaagta    6660
tggcaataac ccactcacac caacaactaa ttctgattat cgtcaacctg gtaatgcatt    6720
tgatttcttg ctagccaacg acgtggataa ttctaatcct gttgtgcaag ctgaaaactt    6780
aaactggtta cattacttaa tgaactttgg caccatcact gcgggtcaag atgacgctaa    6840
ttttgatagt attcgtattg acgctgtcga ctttattcat aatgatacaa tccaacgtac    6900
ttatgattat cttcgtgatg cttatcaagt gcaacaaagt gaagccaaag caaaccagca    6960
catttcattg gttgaagctg gcttagacgc aggtacatca acgattcata atgatgcgtt    7020
aattgagtca aacctccgtg aagcagcgac attgtcgtta acaaatgaac ctggtaaaaa    7080
taaaccattg acgaatatgc tacaagacgt tgacggcggt acgcttatca ccgaccatac    7140
gcagaatagt acagaaaatc aggcgacacc aaactattca attattcacg cgcacgataa    7200
aggtgtgcaa gaaaaagtag gtgcagccat tactgatgct actggtgctg attggacgaa    7260
ctttacagat gaacagttaa aagccggatt agagctattc tataaggatc agcgcgcaac    7320
aaacaaaaag tataatagtt ataacatacc aagtatttat gccctgatgt tgacaaacaa    7380
agatactgtt cctcgtatgt attatgggga tatgtatcaa gatgacggac agtatatggc    7440
aaacaagagt atctactatg atgccttagt gtcattaatg acggctcgta aaagctatgt    7500
cagcggtggt caaactatga gtgttgacaa tcatggtttg ttgaagagtg tccgttttgg    7560
aaaagatgcg atgacagcta atgatttagg tacatcagct acgcgtactg agggtcttgg    7620
tgtcattatt ggtaatgatc caaagttgca acttaatgat tcggataaag tgacactgga    7680
tatgggtgca gcacataaaa atcaaaagta tcgcgcagtt atcttaacaa cacgtgatgg    7740
tttggcaacc tttaattcag atcaagcacc aacagcttgg acaaacgatc aaggaacgtt    7800
aacattctca aatcaagaga ttaacgggca agacaataca caaattcgtg gtgttgctaa    7860
tccgcaagtt tctggttatc tagctgtttg ggtgcctgtg ggtgcatcag acaatcaaga    7920
tgcccgtaca gcagcaacga caacagaaaa tcatgatggt aaagtattac actcgaatgc    7980
ggcattagat tctaacctta tttatgaagg tttctctaac ttccaaccta aggcaacaac    8040
gcatgatgaa cttacgaacg ttgtaattgc taaaaatgcc gatgtcttca ataattgggg    8100
tattacgagt tttgaaatgg caccacagta ccgttcaagt ggggaccata cattcttgga    8160
ttcaacgatt gataatggtt atgccttcac tgatcgctat gacttaggtt tcaatacacc    8220
aacaaagtat ggcactgatg gtgatttgcg tgcaacgatt caagcgctac atcatgctaa    8280
```

-continued

```
tatgcaagtt atggctgacg ttgttgataa ccaggtctat aacttacctg gtaaagaagt    8340
tgtttcagca acacgagcag gtgtttatgg taatgacgac gccacgggct ttggaacgca    8400
actctatgtg actaactccg ttggtggtgg tcaataccaa gagaaatatg ctggacaata    8460
cttagaagct ctgaaagcaa agtatccaga cctctttgag ggtaaggcct atgattattg    8520
gtataagaac tatgcaaatg atgggtcaaa tccttactat acattgtcac acggtgaccg    8580
tgaatctatc ccagcagatg ttgctattaa gcaatggtca gctaagtata tgaacggcac    8640
gaacgttttg ggcaatggta tgggttatgt attgaaggat tggcataatg gtcaatattt    8700
caagcttgat ggtgataaat caacattacc tcaaatttaa tttattttga tagggaacga    8760
ttatcttatc aaattgtagt gacaaaagtc gcagatattg aatccaatat ctgcgacttt    8820
tcgtctgtaa agctatgcta taataacgtt atgacaaaag aaaattattt taaagttggc    8880
acaattgtca cacccacgg tattcgtggc gaagtgaaga ttatggatat c              8931
```

<210> SEQ ID NO 6
<211> LENGTH: 17
<212> TYPE: PRT
<213> ORGANISM: Leuconostoc mesenteroides
<400> SEQUENCE: 6

Ala Asn Trp Asn Ile Asp Ser Glu Ser Lys Gly Asn Asp His Leu Gln
 1               5                  10                  15

Gly

<210> SEQ ID NO 7
<211> LENGTH: 24
<212> TYPE: PRT
<213> ORGANISM: Leuconostoc mesenteroides
<400> SEQUENCE: 7

Gly Gly Tyr Glu Met Leu Leu Ala Asn Asp Val Asp Asn Ser Asn Pro
 1               5                  10                  15

Val Val Gln Ala Glu Gln Leu Asn
            20

<210> SEQ ID NO 8
<211> LENGTH: 21
<212> TYPE: PRT
<213> ORGANISM: Leuconostoc mesenteroides
<400> SEQUENCE: 8

Ala Asn Phe Asp Gly Tyr Arg Val Asp Ala Val Asp Asn Val Asp Ala
 1               5                  10                  15

Asp Leu Leu Gln Ile
            20

<210> SEQ ID NO 9
<211> LENGTH: 12
<212> TYPE: PRT
<213> ORGANISM: Leuconostoc mesenteroides
<400> SEQUENCE: 9

His Ile Ser Ile Leu Glu Asp Trp Asp Asn Asn Asp
 1               5                  10

<210> SEQ ID NO 10
<211> LENGTH: 15
<212> TYPE: PRT

<213> ORGANISM: Leuconostoc mesenteroides

<400> SEQUENCE: 10

Tyr Ala Phe Ile Arg Ala His Asp Ser Glu Val Gln Thr Val Ile
1               5                   10                  15

<210> SEQ ID NO 11
<211> LENGTH: 8
<212> TYPE: PRT
<213> ORGANISM: Leuconostoc mesenteroides

<400> SEQUENCE: 11

Asp Trp Val Pro Asp Gln Ile Tyr
1               5

<210> SEQ ID NO 12
<211> LENGTH: 19
<212> TYPE: PRT
<213> ORGANISM: Leuconostoc mesenteroides

<400> SEQUENCE: 12

Phe Ile Trp Asn Lys Asp Ser Glu Tyr His Gly Gly Gly Asp Ala Trp
1               5                   10                  15

Phe Gln Gly

<210> SEQ ID NO 13
<211> LENGTH: 24
<212> TYPE: PRT
<213> ORGANISM: Leuconostoc mesenteroides

<400> SEQUENCE: 13

Asn Ala Phe Asp Phe Leu Leu Ala Asn Asp Val Asp Asn Ser Asn Pro
1               5                   10                  15

Val Val Gln Ala Glu Asn Leu Asn
            20

<210> SEQ ID NO 14
<211> LENGTH: 21
<212> TYPE: PRT
<213> ORGANISM: Leuconostoc mesenteroides

<400> SEQUENCE: 14

Ala Asn Phe Asp Ser Ile Arg Ile Asp Ala Val Asp Phe Ile His Asn
1               5                   10                  15

Asp Thr Ile Gln Arg
            20

<210> SEQ ID NO 15
<211> LENGTH: 8
<212> TYPE: PRT
<213> ORGANISM: Leuconostoc mesenteroides

<400> SEQUENCE: 15

His Ile Ser Leu Val Glu Ala Gly
1               5

<210> SEQ ID NO 16
<211> LENGTH: 15
<212> TYPE: PRT
<213> ORGANISM: Leuconostoc mesenteroides

<400> SEQUENCE: 16

Tyr Ser Ile Ile His Ala His Asp Lys Gly Val Gln Glu Lys Val

```
<210> SEQ ID NO 17
<211> LENGTH: 8
<212> TYPE: PRT
<213> ORGANISM: Leuconostoc mesenteroides

<400> SEQUENCE: 17

Asp Val Val Asp Asn Gln Val Tyr
 1               5

<210> SEQ ID NO 18
<211> LENGTH: 7
<212> TYPE: PRT
<213> ORGANISM: Leuconostoc mesenteroides

<400> SEQUENCE: 18

Phe Tyr Phe Glu Ser Gly Lys
 1               5

<210> SEQ ID NO 19
<211> LENGTH: 8
<212> TYPE: PRT
<213> ORGANISM: Leuconostoc mesenteroides

<400> SEQUENCE: 19

Phe Glu Ser Gln Asn Asn Asn Pro
 1               5

<210> SEQ ID NO 20
<211> LENGTH: 21
<212> TYPE: DNA
<213> ORGANISM: Artificial Sequence
<220> FEATURE:
<223> OTHER INFORMATION: Synthetic PCR primer sequence

<400> SEQUENCE: 20
ttytayttyg artcaggsaa r                                          21

<210> SEQ ID NO 21
<211> LENGTH: 21
<212> TYPE: DNA
<213> ORGANISM: Artificial Sequence
<220> FEATURE:
<223> OTHER INFORMATION: Synthetic PCR primer sequence

<400> SEQUENCE: 21
ttytayttyg aragcggsaa r                                          21

<210> SEQ ID NO 22
<211> LENGTH: 24
<212> TYPE: DNA
<213> ORGANISM: Artificial Sequence
<220> FEATURE:
<223> OTHER INFORMATION: Synthetic PCR primer sequence

<400> SEQUENCE: 22
kggrttrttr ttttgtgayt caaa                                       24

<210> SEQ ID NO 23
<211> LENGTH: 24
<212> TYPE: DNA
<213> ORGANISM: Artificial Sequence
<220> FEATURE:
<223> OTHER INFORMATION: Synthetic PCR primer sequence
```

```
<400> SEQUENCE: 23
kggrttrttr ttttggctyt caaa                                              24

<210> SEQ ID NO 24
<211> LENGTH: 30
<212> TYPE: DNA
<213> ORGANISM: Artificial Sequence
<220> FEATURE:
<223> OTHER INFORMATION: Synthetic PCR primer sequence

<400> SEQUENCE: 24
ccctttacaa gctgattttg cttatctgcg                                        30

<210> SEQ ID NO 25
<211> LENGTH: 32
<212> TYPE: DNA
<213> ORGANISM: Artificial Sequence
<220> FEATURE:
<223> OTHER INFORMATION: Synthetic PCR primer sequence

<400> SEQUENCE: 25
gggtcaaatc cttactatac attgtcacac gg                                     32

<210> SEQ ID NO 26
<211> LENGTH: 45
<212> TYPE: DNA
<213> ORGANISM: Artificial Sequence
<220> FEATURE:
<223> OTHER INFORMATION: Synthetic PCR primer sequence

<400> SEQUENCE: 26
agttgtatga gagacatgag ggtaatttgt gaccgtaaaa aattg                       45

<210> SEQ ID NO 27
<211> LENGTH: 46
<212> TYPE: DNA
<213> ORGANISM: Artificial Sequence
<220> FEATURE:
<223> OTHER INFORMATION: Synthetic PCR primer sequence

<400> SEQUENCE: 27
atttgaggta atgttgattt atcaccatca agcttgaata ttgacc                      46

<210> SEQ ID NO 28
<211> LENGTH: 30
<212> TYPE: DNA
<213> ORGANISM: Artificial Sequence
<220> FEATURE:
<223> OTHER INFORMATION: Synthetic PCR primer sequence

<400> SEQUENCE: 28
gccatggcaa atacgattgc agttgacacg                                        30

<210> SEQ ID NO 29
<211> LENGTH: 31
<212> TYPE: DNA
<213> ORGANISM: Artificial Sequence
<220> FEATURE:
<223> OTHER INFORMATION: Synthetic PCR primer sequence

<400> SEQUENCE: 29
gccatggacg gtaaaaccta ttttcttgac g                                      31

<210> SEQ ID NO 30
<211> LENGTH: 27
```

```
<212> TYPE: DNA
<213> ORGANISM: Artificial Sequence
<220> FEATURE:
<223> OTHER INFORMATION: Synthetic PCR primer sequence

<400> SEQUENCE: 30
tccatgggtg aaaaaacaag caccggc                                             27

<210> SEQ ID NO 31
<211> LENGTH: 23
<212> TYPE: DNA
<213> ORGANISM: Artificial Sequence
<220> FEATURE:
<223> OTHER INFORMATION: Synthetic PCR primer sequence

<400> SEQUENCE: 31
accatggata tgtctactaa tgc                                                 23

<210> SEQ ID NO 32
<211> LENGTH: 21
<212> TYPE: DNA
<213> ORGANISM: Artificial Sequence
<220> FEATURE:
<223> OTHER INFORMATION: Synthetic PCR primer sequence

<400> SEQUENCE: 32
taactgttta ggcaagaatc c                                                   21

<210> SEQ ID NO 33
<211> LENGTH: 27
<212> TYPE: DNA
<213> ORGANISM: Artificial Sequence
<220> FEATURE:
<223> OTHER INFORMATION: Synthetic PCR primer sequence

<400> SEQUENCE: 33
taatgtatta gtgaataagt attcacc                                             27

<210> SEQ ID NO 34
<211> LENGTH: 24
<212> TYPE: DNA
<213> ORGANISM: Artificial Sequence
<220> FEATURE:
<223> OTHER INFORMATION: Synthetic PCR primer sequence

<400> SEQUENCE: 34
aatttgaggt aatgttgatt tatc                                                24

<210> SEQ ID NO 35
<211> LENGTH: 6
<212> TYPE: PRT
<213> ORGANISM: Artificial Sequence
<220> FEATURE:
<223> OTHER INFORMATION: Consensus sequence derived from Leuconostoc
      mesenteroides

<400> SEQUENCE: 35

Phe Ile His Asn Asp Thr
1               5

<210> SEQ ID NO 36
<211> LENGTH: 7
<212> TYPE: PRT
<213> ORGANISM: Artificial Sequence
<220> FEATURE:
<223> OTHER INFORMATION: Consensus sequence derived from Leuconostoc
      mesenteroides
```

-continued

<400> SEQUENCE: 36

Lys Gly Val Gln Glu Lys Val
1               5

<210> SEQ ID NO 37
<211> LENGTH: 7
<212> TYPE: PRT
<213> ORGANISM: Artificial Sequence
<220> FEATURE:
<223> OTHER INFORMATION: Consensus sequence derived from Leuconostoc
      mesenteroides

<400> SEQUENCE: 37

Asn Val Asp Ala Asp Leu Leu
1               5

<210> SEQ ID NO 38
<211> LENGTH: 7
<212> TYPE: PRT
<213> ORGANISM: Artificial Sequence
<220> FEATURE:
<223> OTHER INFORMATION: Consensus sequence derived from Leuconostoc
      mesenteroides

<400> SEQUENCE: 38

Ser Glu Val Gln Thr Val Ile
1               5

<210> SEQ ID NO 39
<211> LENGTH: 32
<212> TYPE: PRT
<213> ORGANISM: Artificial Sequence
<220> FEATURE:
<223> OTHER INFORMATION: Consensus sequence derived from Leuconostoc
      mesenteroides
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid

<400> SEQUENCE: 39

Trp Trp Tyr Phe Asn Xaa Asp Gly Gln Ala Ala Thr Gly Leu Gln Thr
1               5                   10                  15

Ile Asp Gly Gln Thr Val Phe Asp Asp Asn Gly Xaa Gln Val Lys Gly
            20                  25                  30

<210> SEQ ID NO 40
<211> LENGTH: 48
<212> TYPE: PRT
<213> ORGANISM: Artificial Sequence
<220> FEATURE:
<223> OTHER INFORMATION: Consensus sequence derived from Leuconostoc
      mesenteroides

<400> SEQUENCE: 40

Val Asn Gly Lys Thr Tyr Tyr Phe Gly Ser Asp Gly Thr Ala Gln Thr
1               5                   10                  15

Gln Ala Asn Pro Lys Gly Gln Thr Phe Lys Asp Gly Ser Gly Val Leu
            20                  25                  30

Arg Phe Tyr Asn Leu Glu Gly Gln Tyr Val Ser Gly Ser Gly Trp Tyr
            35                  40                  45

<210> SEQ ID NO 41
<211> LENGTH: 20
<212> TYPE: PRT
<213> ORGANISM: Artificial Sequence
<220> FEATURE:
<223> OTHER INFORMATION: Consensus sequence derived from Leuconostoc
      mesenteroides

<400> SEQUENCE: 41

Asp Gly Lys Ile Tyr Phe Phe Asp Pro Asp Ser Gly Glu Val Val Lys
1               5                   10                  15

Asn Arg Phe Val
            20

<210> SEQ ID NO 42
<211> LENGTH: 14
<212> TYPE: PRT
<213> ORGANISM: Artificial Sequence
<220> FEATURE:
<223> OTHER INFORMATION: Consensus sequence derived from Leuconostoc
      mesenteroides

<400> SEQUENCE: 42

Gly Gly Val Val Lys Asn Ala Asp Gly Thr Tyr Ser Lys Tyr
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Consensus sequence derived from Leuconostoc
      mesenteroides
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(11)
<223> OTHER INFORMATION: Xaa can be any naturally occurring amino acid

<400> SEQUENCE: 43

Tyr Tyr Phe Xaa Ala Xaa Gln Gly Xaa Xaa Xaa Leu
1               5                   10

<210> SEQ ID NO 44
<211> LENGTH: 16
<212> TYPE: PRT
<213> ORGANISM: Artificial Sequence
<220> FEATURE:
<223> OTHER INFORMATION: Synthetic peptide

<400> SEQUENCE: 44

Tyr Tyr Phe Asp Asp Lys Gly Asn Gly Glu Tyr Cys Phe Thr Asn Thr
1               5                   10                  15

<210> SEQ ID NO 45
<211> LENGTH: 38
<212> TYPE: PRT
<213> ORGANISM: Leuconostoc mesenteroides

<400> SEQUENCE: 45

Met Phe Met Ile Lys Glu Arg Asn Val Arg Lys Lys Leu Tyr Lys Ser

```
                1               5                   10                  15
Gly Lys Ser Trp Val Ile Gly Gly Leu Ile Leu Ser Thr Ile Met Leu
            20                  25                  30

Ser Met Thr Ala Thr Ser
        35

<210> SEQ ID NO 46
<211> LENGTH: 32
<212> TYPE: PRT
<213> ORGANISM: Leuconostoc mesenteroides

<400> SEQUENCE: 46

Met Pro Phe Thr Glu Lys Val Met Arg Lys Lys Leu Tyr Lys Val Gly
1               5                   10                  15

Lys Ser Trp Val Val Gly Gly Val Cys Ala Phe Ala Leu Thr Ala Ser
            20                  25                  30

<210> SEQ ID NO 47
<211> LENGTH: 38
<212> TYPE: PRT
<213> ORGANISM: Leuconostoc mesenteroides

<400> SEQUENCE: 47

Met Lys Gln Gln Glu Thr Val Thr Arg Lys Lys Tyr Lys Ser Gly Lys
1               5                   10                  15

Val Trp Val Ala Ala Ala Thr Ala Phe Ala Val Leu Gly Val Ser Thr
            20                  25                  30

Val Thr Thr Val His Ala
        35

<210> SEQ ID NO 48
<211> LENGTH: 45
<212> TYPE: DNA
<213> ORGANISM: Artificial Sequence
<220> FEATURE:
<223> OTHER INFORMATION: Synthetic oligonucleotide ECHO-dir

<400> SEQUENCE: 48
agttgtatga gagacatgag ggtaatttgt gaccgtaaaa aattg                      45

<210> SEQ ID NO 49
<211> LENGTH: 49
<212> TYPE: DNA
<213> ORGANISM: Artificial Sequence
<220> FEATURE:
<223> OTHER INFORMATION: Synthetic oligonucleotide ECHO-inv-del

<400> SEQUENCE: 49
gtattagtga ataagtattc accattgcat ttatcgtcaa aatagtacg                  49

<210> SEQ ID NO 50
<211> LENGTH: 13
<212> TYPE: PRT
<213> ORGANISM: Leuconostoc mesenteroides

<400> SEQUENCE: 50

Ala Ala Lys Val Val Ala Val Ala Thr Thr Pro Ala Thr
1               5                   10

<210> SEQ ID NO 51
<211> LENGTH: 9
<212> TYPE: PRT
<213> ORGANISM: Leuconostoc mesenteroides
```

<400> SEQUENCE: 51

Pro Val Ala Asp Lys Thr Val Ser Ala
1               5

<210> SEQ ID NO 52
<211> LENGTH: 14
<212> TYPE: PRT
<213> ORGANISM: Leuconostoc mesenteroides

<400> SEQUENCE: 52

Pro Ala Ala Asp Lys Ala Val Asp Thr Thr Ser Ser Thr Thr
1               5                   10

<210> SEQ ID NO 53
<211> LENGTH: 13
<212> TYPE: PRT
<213> ORGANISM: Leuconostoc mesenteroides

<400> SEQUENCE: 53

Pro Ala Thr Asp Lys Ala Val Asp Thr Thr Pro Thr Thr
1               5                   10

<210> SEQ ID NO 54
<211> LENGTH: 13
<212> TYPE: PRT
<213> ORGANISM: Leuconostoc mesenteroides

<400> SEQUENCE: 54

Pro Ala Ala Asp Lys Ala Val Asp Thr Thr Pro Thr Thr
1               5                   10

<210> SEQ ID NO 55
<211> LENGTH: 13
<212> TYPE: PRT
<213> ORGANISM: Leuconostoc mesenteroides

<400> SEQUENCE: 55

Pro Ala Ala Asp Lys Ala Val Asp Thr Thr Pro Thr Thr
1               5                   10

<210> SEQ ID NO 56
<211> LENGTH: 13
<212> TYPE: PRT
<213> ORGANISM: Leuconostoc mesenteroides

<400> SEQUENCE: 56

Pro Ala Ala Asn Lys Ala Val Asp Thr Thr Pro Ala Thr
1               5                   10

<210> SEQ ID NO 57
<211> LENGTH: 12
<212> TYPE: PRT
<213> ORGANISM: Leuconostoc mesenteroides

<400> SEQUENCE: 57

Ala Ala Thr Asp Lys Ala Val Ala Thr Pro Ala Thr
1               5                   10

<210> SEQ ID NO 58
<211> LENGTH: 12
<212> TYPE: PRT
<213> ORGANISM: Leuconostoc mesenteroides

<400> SEQUENCE: 58

```
Pro Ala Ala Asp Lys Leu Ala Asn Thr Thr Ala Thr
1               5                   10

<210> SEQ ID NO 59
<211> LENGTH: 10
<212> TYPE: PRT
<213> ORGANISM: Leuconostoc mesenteroides

<400> SEQUENCE: 59

Asp Lys Ala Val Ala Thr Thr Pro Ala Thr
1               5                   10

<210> SEQ ID NO 60
<211> LENGTH: 7
<212> TYPE: PRT
<213> ORGANISM: Leuconostoc mesenteroides

<400> SEQUENCE: 60

Pro Val Ala Asn Lys Ala Ala
1               5

<210> SEQ ID NO 61
<211> LENGTH: 13
<212> TYPE: PRT
<213> ORGANISM: Leuconostoc mesenteroides
<220> FEATURE:
<221> NAME/KEY: misc_feature
<222> LOCATION: (12)..(12)
<223> OTHER INFORMATION: Xaa can be Ala or Ile

<400> SEQUENCE: 61

Pro Ala Ala Asp Lys Ala Val Asp Thr Thr Pro Xaa Thr
1               5                   10

<210> SEQ ID NO 62
<211> LENGTH: 17
<212> TYPE: PRT
<213> ORGANISM: Leuconostoc mesenteroides

<400> SEQUENCE: 62

Ser Ala Trp Asn Ser Asp Ser Glu Lys Pro Phe Asp Asp His Leu Gln
1               5                   10                  15

Asn

<210> SEQ ID NO 63
<211> LENGTH: 24
<212> TYPE: PRT
<213> ORGANISM: Leuconostoc mesenteroides

<400> SEQUENCE: 63

Gly Gly Tyr Glu Phe Leu Leu Ala Asn Asp Val Asp Asn Ser Asn Pro
1               5                   10                  15

Val Val Gln Ala Glu Gln Leu Asn
            20

<210> SEQ ID NO 64
<211> LENGTH: 21
<212> TYPE: PRT
<213> ORGANISM: Leuconostoc mesenteroides

<400> SEQUENCE: 64

Ala Asn Phe Asp Ser Ile Arg Val Asp Ala Val Asp Asn Val Asp Ala
1               5                   10                  15
```

Asp Leu Leu Gln Ile
            20

<210> SEQ ID NO 65
<211> LENGTH: 12
<212> TYPE: PRT
<213> ORGANISM: Leuconostoc mesenteroides

<400> SEQUENCE: 65

His Leu Ser Ile Leu Glu Ala Trp Ser Asp Asn Asp
1               5                   10

<210> SEQ ID NO 66
<211> LENGTH: 15
<212> TYPE: PRT
<213> ORGANISM: Leuconostoc mesenteroides

<400> SEQUENCE: 66

Tyr Ser Phe Ile Arg Ala His Asp Ser Glu Val Gln Asp Leu Ile
1               5                   10                  15

<210> SEQ ID NO 67
<211> LENGTH: 8
<212> TYPE: PRT
<213> ORGANISM: Leuconostoc mesenteroides

<400> SEQUENCE: 67

Asp Trp Val Pro Asp Gln Met Tyr
1               5

<210> SEQ ID NO 68
<211> LENGTH: 17
<212> TYPE: PRT
<213> ORGANISM: Leuconostoc mesenteroides

<400> SEQUENCE: 68

Pro Gln Trp Asn Gly Glu Ser Glu Lys Pro Tyr Asp Asp His Leu Gln
1               5                   10                  15

Asn

<210> SEQ ID NO 69
<211> LENGTH: 24
<212> TYPE: PRT
<213> ORGANISM: Leuconostoc mesenteroides

<400> SEQUENCE: 69

Gly Gly Tyr Glu Leu Leu Leu Ala Asn Asp Val Asp Asn Ser Asn Pro
1               5                   10                  15

Ile Val Gln Ala Glu Gln Leu Asn
            20

<210> SEQ ID NO 70
<211> LENGTH: 21
<212> TYPE: PRT
<213> ORGANISM: Leuconostoc mesenteroides

<400> SEQUENCE: 70

Ala Asn Phe Asp Ser Ile Arg Val Asp Ala Val Asp Asn Val Asp Ala
1               5                   10                  15

Asp Leu Leu Gln Ile
            20

<210> SEQ ID NO 71

```
<211> LENGTH: 12
<212> TYPE: PRT
<213> ORGANISM: Leuconostoc mesenteroides

<400> SEQUENCE: 71

His Val Ser Ile Val Glu Ala Trp Ser Asp Asn Asp
1               5                   10

<210> SEQ ID NO 72
<211> LENGTH: 15
<212> TYPE: PRT
<213> ORGANISM: Leuconostoc mesenteroides

<400> SEQUENCE: 72

Tyr Ser Phe Ala Arg Ala His Asp Ser Glu Val Gln Asp Leu Ile
1               5                   10                  15

<210> SEQ ID NO 73
<211> LENGTH: 8
<212> TYPE: PRT
<213> ORGANISM: Leuconostoc mesenteroides

<400> SEQUENCE: 73

Asp Trp Val Pro Asp Gln Met Tyr
1               5

<210> SEQ ID NO 74
<211> LENGTH: 21
<212> TYPE: PRT
<213> ORGANISM: Leuconostoc mesenteroides

<400> SEQUENCE: 74

Asn Gln Trp Ser Ile Ala Ser Glu Asn Glu Thr Val Tyr Pro Asn Gln
1               5                   10                  15

Asp His Met Gln Gly
            20

<210> SEQ ID NO 75
<211> LENGTH: 24
<212> TYPE: PRT
<213> ORGANISM: Leuconostoc mesenteroides

<400> SEQUENCE: 75

Ala Gly Tyr Glu Leu Leu Leu Ala Asn Asp Val Asp Asn Ser Asn Pro
1               5                   10                  15

Val Val Gln Ala Glu Gln Leu Asn
            20

<210> SEQ ID NO 76
<211> LENGTH: 21
<212> TYPE: PRT
<213> ORGANISM: Leuconostoc mesenteroides

<400> SEQUENCE: 76

Ala Asn Phe Asp Gly Val Arg Val Asp Ala Val Asp Asn Val Asn Ala
1               5                   10                  15

Asp Leu Leu Gln Ile
            20

<210> SEQ ID NO 77
<211> LENGTH: 12
<212> TYPE: PRT
<213> ORGANISM: Leuconostoc mesenteroides
```

```
<400> SEQUENCE: 77

His Leu Ser Ile Leu Glu Ala Trp Ser Gly Asn Asp
1               5                   10

<210> SEQ ID NO 78
<211> LENGTH: 15
<212> TYPE: PRT
<213> ORGANISM: Leuconostoc mesenteroides

<400> SEQUENCE: 78

Tyr Val Phe Ile Arg Ala His Asp Ser Glu Val Gln Thr Arg Ile
1               5                   10                  15

<210> SEQ ID NO 79
<211> LENGTH: 8
<212> TYPE: PRT
<213> ORGANISM: Leuconostoc mesenteroides

<400> SEQUENCE: 79

Asp Leu Val Pro Asn Gln Leu Tyr
1               5

<210> SEQ ID NO 80
<211> LENGTH: 17
<212> TYPE: PRT
<213> ORGANISM: Leuconostoc mesenteroides

<400> SEQUENCE: 80

Pro Gln Trp Asn Glu Thr Ser Glu Asp Met Ser Asn Asp His Leu Gln
1               5                   10                  15

Asn

<210> SEQ ID NO 81
<211> LENGTH: 24
<212> TYPE: PRT
<213> ORGANISM: Leuconostoc mesenteroides

<400> SEQUENCE: 81

Gly Gly Phe Glu Leu Leu Leu Ala Asn Asp Val Asp Asn Ser Asn Pro
1               5                   10                  15

Val Val Gln Ala Glu Gln Leu Asn
            20

<210> SEQ ID NO 82
<211> LENGTH: 21
<212> TYPE: PRT
<213> ORGANISM: Leuconostoc mesenteroides

<400> SEQUENCE: 82

Ala Asn Phe Asp Gly Ile Arg Val Asp Ala Val Asp Asn Val Asp Ala
1               5                   10                  15

Asp Leu Leu Gln Ile
            20

<210> SEQ ID NO 83
<211> LENGTH: 12
<212> TYPE: PRT
<213> ORGANISM: Leuconostoc mesenteroides

<400> SEQUENCE: 83

His Leu Ser Ile Leu Glu Asp Trp Ser His Asn Asp
1               5                   10
```

```
<210> SEQ ID NO 84
<211> LENGTH: 15
<212> TYPE: PRT
<213> ORGANISM: Leuconostoc mesenteroides

<400> SEQUENCE: 84

Tyr Ser Phe Val Arg Ala His Asp Ser Glu Val Gln Thr Val Ile
1               5                   10                  15

<210> SEQ ID NO 85
<211> LENGTH: 8
<212> TYPE: PRT
<213> ORGANISM: Leuconostoc mesenteroides

<400> SEQUENCE: 85

Asp Trp Val Pro Asp Gln Ile Tyr
1               5

<210> SEQ ID NO 86
<211> LENGTH: 17
<212> TYPE: PRT
<213> ORGANISM: Leuconostoc mesenteroides

<400> SEQUENCE: 86

Pro Asn Trp Asn Ile Asp Ser Glu Ala Lys Gly Asp Asp His Leu Gln
1               5                   10                  15

Gly

<210> SEQ ID NO 87
<211> LENGTH: 24
<212> TYPE: PRT
<213> ORGANISM: Leuconostoc mesenteroides

<400> SEQUENCE: 87

Gly Gly Phe Glu Leu Leu Leu Ala Asn Asp Val Asp Asn Ser Asn Pro
1               5                   10                  15

Val Val Gln Ala Glu Gln Leu Asn
            20

<210> SEQ ID NO 88
<211> LENGTH: 21
<212> TYPE: PRT
<213> ORGANISM: Leuconostoc mesenteroides

<400> SEQUENCE: 88

Ala Asn Phe Asp Gly Tyr Arg Val Asp Ala Val Asp Asn Val Asp Ala
1               5                   10                  15

Asp Leu Leu Gln Ile
            20

<210> SEQ ID NO 89
<211> LENGTH: 12
<212> TYPE: PRT
<213> ORGANISM: Leuconostoc mesenteroides

<400> SEQUENCE: 89

Ile Tyr Gln Phe Trp Lys Thr Gly Glu Met Lys Ile
1               5                   10

<210> SEQ ID NO 90
<211> LENGTH: 15
<212> TYPE: PRT
<213> ORGANISM: Leuconostoc mesenteroides
```

```
<400> SEQUENCE: 90

Tyr Ser Phe Ile Arg Ala His Asp Ser Glu Val Gln Thr Ile Ile
1               5                   10                  15

<210> SEQ ID NO 91
<211> LENGTH: 8
<212> TYPE: PRT
<213> ORGANISM: Leuconostoc mesenteroides

<400> SEQUENCE: 91

Asp Trp Val Pro Asp Gln Ile Tyr
1               5

<210> SEQ ID NO 92
<211> LENGTH: 17
<212> TYPE: PRT
<213> ORGANISM: Leuconostoc mesenteroides

<400> SEQUENCE: 92

Pro Gln Trp Asn Met Ser Ser Glu Asp Pro Lys Asn Asp His Leu Gln
1               5                   10                  15

Asn

<210> SEQ ID NO 93
<211> LENGTH: 24
<212> TYPE: PRT
<213> ORGANISM: Leuconostoc mesenteroides

<400> SEQUENCE: 93

Gly Gly Phe Glu Leu Leu Leu Ala Asn Asp Val Asp Asn Ser Asn Pro
1               5                   10                  15

Val Val Gln Ser Glu Gln Leu Asn
            20

<210> SEQ ID NO 94
<211> LENGTH: 21
<212> TYPE: PRT
<213> ORGANISM: Leuconostoc mesenteroides

<400> SEQUENCE: 94

Ala Asn Phe Asp Gly Ile Arg Val Asp Ala Val Asp Asn Val Asp Ala
1               5                   10                  15

Asp Leu Leu Gln Ile
            20

<210> SEQ ID NO 95
<211> LENGTH: 12
<212> TYPE: PRT
<213> ORGANISM: Leuconostoc mesenteroides

<400> SEQUENCE: 95

His Leu Ser Ile Leu Glu Asp Trp Ser His Asn Asp
1               5                   10

<210> SEQ ID NO 96
<211> LENGTH: 15
<212> TYPE: PRT
<213> ORGANISM: Leuconostoc mesenteroides

<400> SEQUENCE: 96

Tyr Ser Phe Val Arg Ala His Asp Ser Glu Val Gln Thr Val Ile
1               5                   10                  15
```

```
<210> SEQ ID NO 97
<211> LENGTH: 8
<212> TYPE: PRT
<213> ORGANISM: Leuconostoc mesenteroides

<400> SEQUENCE: 97

Asp Trp Val Pro Asp Gln Ile Tyr
1               5

<210> SEQ ID NO 98
<211> LENGTH: 20
<212> TYPE: PRT
<213> ORGANISM: Leuconostoc mesenteroides

<400> SEQUENCE: 98

Ala Asn Trp Asn Lys Gln Thr Glu Asp Glu Ala Phe Asp Gly Leu Gln
1               5                   10                  15

Trp Leu Gln Gly
            20

<210> SEQ ID NO 99
<211> LENGTH: 24
<212> TYPE: PRT
<213> ORGANISM: Leuconostoc mesenteroides

<400> SEQUENCE: 99

Lys Gly Ser Glu Phe Leu Leu Ala Asn Asp Ile Asp Asn Ser Asn Pro
1               5                   10                  15

Ile Val Gln Ala Glu Gln Leu Asn
            20

<210> SEQ ID NO 100
<211> LENGTH: 21
<212> TYPE: PRT
<213> ORGANISM: Leuconostoc mesenteroides

<400> SEQUENCE: 100

Ala Asn Phe Asp Gly Ile Arg Val Asp Ala Val Asp Asn Val Asp Ala
1               5                   10                  15

Asp Leu Leu Lys Ile
            20

<210> SEQ ID NO 101
<211> LENGTH: 12
<212> TYPE: PRT
<213> ORGANISM: Leuconostoc mesenteroides

<400> SEQUENCE: 101

His Leu Ser Ile Leu Glu Asp Trp Asn Gly Lys Asp
1               5                   10

<210> SEQ ID NO 102
<211> LENGTH: 15
<212> TYPE: PRT
<213> ORGANISM: Leuconostoc mesenteroides

<400> SEQUENCE: 102

Tyr Ser Phe Val Arg Ala His Asp Tyr Asp Ala Gln Asp Pro Ile
1               5                   10                  15

<210> SEQ ID NO 103
<211> LENGTH: 8
```

```
<212> TYPE: PRT
<213> ORGANISM: Leuconostoc mesenteroides

<400> SEQUENCE: 103

Asp Trp Val Pro Asp Gln Ile Tyr
1               5
```

NUCLEIC ACID MOLECULES CODING FOR A DEXTRAN-SACCHARASE CATALYSING THE SYNTHESIS OF DEXTRAN WITH α 1,2 OSIDIC SIDECHAINS

The present invention relates to the field of glycotechnology, more particularly to the synthesis of oligosaccharides or oligosides with a prebiotic, therapeutic or diagnostic effect.

The present invention pertains to nucleic acid molecules encoding an enzyme having a glycosyltransferase activity catalyzing the synthesis of dextrans or oligosides carrying $\alpha(1\rightarrow2)$ osidic type linkages.

The invention also pertains to enzymes synthesized by the nucleic acids of the invention, and to their expression systems in prokaryotic or eukaryotic cells. Finally, they pertain to the use of said enzymes in the production of oligosaccharides in foodstuffs, or as an active principle in therapeutic and/or cosmetic products.

Oligosides and heterooligosides act as recognition and effector signals in both animals and plants (as oligosaccharines) by specifically binding to lectins, glycosyltransferases, glycosidases, adhesion molecules etc. The antigenic determinants of blood groups are osidics and our defense against many pathogenic bacteria is directed against osidic structures of the bacterial envelope. Further, one of the major reasons for xenograft rejection is the existence of osidic structures belonging to each species. Such properties, and the knowledge acquired in recent years regarding glycosyltransferases and lectins, contribute to making certain oligosides the candidates of choice for therapeutic or prophylactic treatment of disorders linked to the microbiological equilibrium of various organs such as the intestine or skin. As an example, oligosides constitute an interesting alternative to the use of micro-organisms and antibiotics in regulating the composition of intestinal flora (prebiotic effect). Certain oligosides can be considered to be "soluble fiber" when they are not metabolized by human and animal digestive enzymes; on reaching the colon, they interact with the microbial flora and specifically affect the growth and adhesion of certain species. If they are incorporated into food in low doses (less than 1%), certain osidic molecules improve health and stimulate weight gain in animals.

A review of different glycosyltransferases, their structure and their activity, has been carried out by Vincent Monchois et al (1). Briefly:

a) it appears that the structure of the glycosyltransferases and/or dextransucrases studied is highly conserved and is constituted, starting from the amino part of the protein, by a signal sequence, a variable domain, a catalytic domain and a glucan binding domain.

b) glucooligosides (GOS) can be synthesized by glycosyltransferases such as dextransucrases from cheaper substrates such as saccharose and in the presence of a glucose accepting sugar. Other substrates such as α-D-fluoroglucose, para-nitrophenyl-α-D-glucopyranoside, α-D-glucopyranoside-α-D-sorbofuranoside or 4-O-α-D-galactopyranosylsucrose can also be used.

Starting from the substrate, such enzymes catalyze the transfer of glucose units onto acceptor molecules. In the presence of a glucose acceptor such as maltose or isomaltose, glycosyltransferases catalyze the synthesis of low molecular weight oligosaccharides primarily comprising chains with 3 to 7 glucoses, in accordance with the reaction:

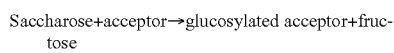

In such cases, enzymes generally have a specificity for the synthesis of osidic bonds in accordance with that forming the donor polymer.

In contrast, in the absence of an acceptor, the enzyme synthesizes high molecular weight dextran type glucans by successive transfer of α-D-glucopyranosyl units from saccharose in accordance with the reaction:

c) The structures and function of glucans or oligosides synthesized by glycosyltransferases depends on the producing bacterial strain.

Throughout the present text, the generic term "glycosyltransferases" is used to designate the different enzymes capable of catalyzing the synthesis of glucose polymers from saccharose. They are generally produced by bacterial strains of the *Leuconostoc, Lactococcus, Streptococcus* or *Neisseria* type. The size and structure of the glucans produced depends on the producing strain.

The glucose units are coupled by $\alpha(1\rightarrow6)$ osidic bonds as in dextran, by $\alpha(1\rightarrow3)$ bonds as in the case of mutane, or by alternations of the two types (alternane).

Similarly, the existence and nature of the linkages, their length and position varies depending on the origin of the producing strain.

Glycosyltransferases producing glucans or GOSs containing at least 50% $\alpha(1\rightarrow6)$ bonds are termed dextransucrases. GOSs synthesized by said enzymes may carry $\alpha(1\rightarrow2)$, $\alpha(1\rightarrow3)$ and/or $\alpha(1\rightarrow4)$ linkages. Said dextransucrases are produced by *Leuconostoc mesenteroides* type bacteria.

d) The dextransucrase from *L. mesenteroides* NRRL B-1299 can produce a highly branched dextran the majority of linkages of which are of the $\alpha(1\rightarrow2)$ type. Used in the presence of saccharose and maltose, a glucose acceptor molecule, it results in the formation of GOS some of which have a $\alpha(1\rightarrow2)$ bond at their non-reducing end and others of which have $\alpha(1\rightarrow2)$ linkages on intermediate residues between the ends. For this reason, they resist degradation by enzymes (hydrolases) of the upper digestive tract in man and animals, and are only degraded by bacterial genuses that are capable of fermenting, such as *Bacteroides* and *Bifidobacterium*, considered to be beneficial to the host organism.

An identical phenomenon occurs in the skin, allowing cosmetic applications to be envisaged, since a lack of equilibrium of the cutaneous microbial flora is the root of numerous cosmetic and dermatological problems. For these reasons, they are designated "GOS of interest" in the present text.

Throughout the text, polysaccharides synthesized by the glycosyltransferases of the invention are either high molecular weight dextrans when the reaction is carried out without a glucose acceptor, or oligosides when the reaction is carried out in the presence of a glucose acceptor such as maltose or isomaltose without this necessarily being specified. The functionality of the enzyme is characterized by the nature of the glucose-glucose bonds, $[\alpha(1\rightarrow6), \alpha(1\rightarrow2)]$ or others, and not by the molecular weight of the polysaccharide that is synthesized.

dextransucrases from *L. mesenteroides* already have a number of applications in industry, and in particular those from the NRRL B-1299 strain for which a method for synthesizing GOSs having $\alpha(1\rightarrow2)$ linkages has been described in European patent EP-B1-0 325 872.

Marguerite Dols et al (2) showed that the GOS produced dextransucrases from that strain are in fact a mixture of at least three similar families of molecules differing by the number and position of the $\alpha(1\rightarrow2)$ type linkages, which leads to the hypothesis that different glycosyltransferase type enzymatic activities exist in that bacterial strain.

Because of the industrial interest pertaining to GOSs with α(1→2) linkages as summarized above in the field of prebiotic foodstuffs, in cosmetics or in pharmaceuticals, the present invention aims to isolate and characterize a particular enzyme from among those produced by *L mesenteroides* NRRL B-1299 which more particularly would be involved in the synthesis of oligosides having α(1→2) linkages. The identification and characterization of such an enzyme have the advantage firstly of providing a uniform, reproducible method for producing GOSs of interest and secondly of identifying the essential characteristics of the producer enzyme for said GOSs of interest in order, if appropriate, to improve the performance of the products of the enzymatic reaction as a function of the envisaged use.

The technical problem underlying the present invention is thus to provide an enzyme and hence isolated nucleic acids encoding said enzyme to allow the improved production of GOS having α(1→2) linkages.

The present invention provides a technical solution to the various questions mentioned above by providing a novel dextransucrase, termed DSR-E, encoded by a gene endowed with a novel and unexpected structure (dsrE) capable of catalyzing the synthesis of glucans or oligosaccharides containing α(1→2) linkages.

Between the date of filing of the priority document, French patent number 0103631 in which the dextransucrase of the invention was termed DSR-D, and that of the present application, another dextransucrase, different from the enzyme of the invention, was described and also termed DSR-D. For this reason, in the present patent application, the dextransucrase described, claimed and shown in FIG. 1*b*) is no longer designated DSR-D as in the priority document, but is termed DSR-E. In fact, the DSR-D dextransucrases in said priority document and DSR-E are completely identical.

The term "novel and unexpected structure" means that the organization of the protein differs from that of all other glycosyltransferases described until now (1) with a catalytic domain located upstream of a glucan binding domain, the latter constituting the carboxylic portion of the protein.

The present invention thus concerns an isolated polypeptide having an enzymatic glycosyltransferase activity capable of forming dextrans having α(1→2) linkages, characterized in that it comprises at least one glucan binding domain and a catalytic activity domain located downstream of the glucan binding domain. The term "located downstream" means the fact that the amine portion of the sequence with catalytic activity or catalytic domain is proximal to the carboxylic portion of the glucan binding domain. These two domains can be immediately contiguous or, in contrast, they may be separated by a variable domain.

The glycosyltransferase of the invention preferably comprises a signal peptide.

In one implementation of the invention, the glycosyltransferase comprises two catalytic domains located either side of the glucan binding domain.

The presence of a domain with catalytic activity in the carboxylic portion of the enzyme is an essential characteristic of the latter in its capacity to form osidic α(1→2) bonds. In fact, as will be shown in the experiments described below, deletion of this domain results in an enzyme having at least two catalytic domains results in the production of glucans or oligosides essentially having α(1→6) type osidic bonds and free of α(1→2) type bonds.

More precisely, the catalytic domain, as long as it is located downstream of a glucan binding domain, allows the synthesis of oligosides containing α(1→2) bonds.

Further, the experiments described below demonstrate that the specificity of the dextransucrase DSR-E function, namely its capacity to catalyze the formation of α(1→2) osidic bonds, can be attributed not to the concomitant presence of two catalytic domains but rather to the concatenation of a glucan binding domain and a catalytic domain, and more particularly the CD2 catalytic domain.

A comparative analysis of the different glycosyltransferases including dextransucrases has demonstrated a very high degree of conservation of their catalytic domain.

The catalytic domain located in the carboxy-terminal portion of the glycosyltransferase of the invention has a sequence having at least 44% identity and 55% similarity with the catalytic domains of the other analyzed glycosyltransferases. In particular, the catalytic domain in the carboxylic portion of the glycosyltransferase of the invention has at least 65% identity and at least 80% similarity with the SEQ ID No: 1, the catalytic triad Asp/Glu/Asp in respective positions 230/268/342 being conserved.

Throughout the text, the term "X %" similarity" with respect to a reference sequence means that X % of the amino acids are identical or modified by conservative substitution as defined in the ClustalW amino acid alignment software (http:///bioweb.pasteur.fr/docs/doc-gensoft/clustalw//) and that (100-X)% can be deleted, substituted by other amino acids, or that (100-X)% can be added to the reference sequence. A particular primary structure of the enzyme of the invention is shown in SEQ ID No: 2 which represent a sequence of 2835 amino acids of a dextransucrase of *L. mesenteroides* NRRL B-1299.

This dextransucrase, denoted DSR-E, like most glycosyltransferases and dextransucrases, has a signal sequence, a variable domain of low conservation, a highly conserved catalytic domain (CD1), a glucan binding domain (GBD) and a second catalytic domain (CD2) in the carboxylic portion of the protein. DSR-E is the first glycosyltransferase analyzed and has two catalytic domains, in the configuration shown in FIG. 1*b*). It is also the first glycosyltransferase the catalytic domain of which is located in the carboxylic portion of the protein.

FIG. 1*b*) also shows that the glucan binding domain is substantially longer than that described above for known dextransucrases; thus, a further characteristic of the enzymes of the invention is the size of this domain which is over 500 amino acids.

A comparison and analysis of the DSR-E sequence with the sequences of the glycosyltransferases or dextransucrases that have already been described (1), and the means used to this end are indicated in Example 2 detailed below. It clearly shows that while the existence of two catalytic domains substantially differentiates DSR-E from other enzymes, in contrast the sequences of said domains are substantially conserved. In particular, the amino acids necessary for catalytic activity are conserved in the second catalytic domain, namely the triad Asp/Glu/Asp located in respective positions 2210/2248/2322 of SEQ ID No: 2.

Thus, the invention also concerns any isolated polypeptide having a catalytic glycosyltransferase activity that is capable of forming dextrans or oligosaccharides having α(1→2) linkages as obtained by modification, substitution, insertion or deletion of amino acid sequences but comprising sequences having at least 80% and preferably at least 90% similarity with the following sequences of SEQ ID No: 2:

| | |
|---|---|
| 423-439 | 2120-2138 |
| 478-501 | 2161-2184 |
| 519-539 | 2202-2214 |
| 560-571 | 2243-2250 |
| 631-645 | 2315-2322 |
| 1014-1021 | 2689-2696 |

Preferably, finally, a polypeptide with catalytic activity of the invention contains the following amino acids:

W in positions 425 and 2122;

E in positions 430, 565 and 2127, 2248;

D in positions 487, 489, 527, 638, 2170, 2172, 2210 and 2322;

H in position 637 and 2321;

Q in position 1019 and 2694.

The polypeptides with glycosyltransferase activity that can form osidic $\alpha(1 \rightarrow 2)$ bonds can be in the isolated form or, in contrast, integrated into a larger protein such as a fusion protein. It may be advantageous to include sequences having another function, such as a specific tag sequence of a ligand that can facilitate purification. These tag sequences can be of the following types: GST (glutathione-S-transferase), intein-CBD (chitin-binding domain) (sold by New England Biolabs, http://www.neb.com), MBD (maltose binding domain), polypeptides containing contiguous histidine residues that can facilitate purification of the polypeptide with which it is fused. The skilled person could design any other fusion protein that could associate the function of the DSR-E of the invention with another function, a non limiting example being a sequence increasing the stability of the enzyme produced by expression in a recombinant host or a sequence that can increase the specificity or efficacy of action of said enzyme, or a sequence aimed at associating another connected enzymatic activity.

Such fusion proteins also fall within the scope of the invention provided that they contain the CD2 domain of the glucan binding site. In the same manner, fragments of SEQ ID No: 2, comprising at least SEQ ID No: 1 and the glucan binding domain, alone or integrated into a larger polypeptide forms part of the invention, as long as the enzymatic activity of the dextransucrase is conserved.

Variations of the polypeptide sequences defined above also form part of the invention. In addition to the polypeptides obtained by conservative substitution of the amino acids defined above, the variations include polypeptides the enzymatic activity of which is improved, for example by directed or random mutagenesis, by DNA shuffling, or by duplication of the CD2 catalytic domain.

The particular structure of this enzyme identified in the present invention results from a process comprising:

a) identifying and isolating dextransucrase from *L mesenteroides* catalyzing the production of GOSs of interest carrying $\alpha(1 \rightarrow 2)$ linkages;

b) sequencing the enzyme fragments;

c) synthesizing amplification primers that can amplify the gene corresponding to the producing strain or fragments thereof;

d) sequencing the amplified fragments;

e) cloning in specific vectors and their expression in appropriate hosts.

The features of the method employed are given in detail in the experimental section below. The first step consists of separating the proteins by polyacrylamide gel electrophoresis and identifying bands having a dextransucrase activity by an in situ enzymatic reaction in the presence of substrate and acceptor. The nature of the GOSs synthesized is then identified for each band by HPLC analysis using the methods described in (1). The retention time for the oligosides in HPLC depends on the nature and organization of their osidic bonds. In particular, it is possible to distinguish between those constituted by residues having $\alpha(1 \rightarrow 6)$ bonds, having $\alpha(1 \rightarrow 6)$ bonds with a $\alpha(1 \rightarrow 2)$ linkage at the nonreducing end of the molecule, and the desired compounds having a linear $\alpha(1 \rightarrow 6)$ chain with $\alpha(1 \rightarrow 2)$ linkages.

The inventors therefore isolated and identified dextransucrase from *L. mesenteroides* NRRL B-1299 producing GOSs of interest.

A reverse engineering process carried out in steps b) to e) above then provide the nucleotide sequence encoding the enzyme, allowing industrial scale production and, if appropriate, allowing it to be modified, improving its performance using techniques that are available to the skilled person. As an example, directed or random mutagenesis or DNA shuffling can be cited (3).

The invention also pertains to an isolated nucleic acid molecule encoding an enzyme with glycosyltransferase activity that can form dextrans or oligosides having $\alpha(1 \rightarrow 2)$ linkages and comprising at least one sequence encoding a glucan binding domain, and at least one nucleotide sequence encoding a catalytic domain located on the 3' side of the foregoing, said sequence encoding a catalytic domain having at least 50% and preferably at least 70% similarity with SEQ ID No: 3.

The term "similarity" means that for the same reading frame, a given triplet is translated by the same amino acid. Thus, this term includes modifications to bases resulting in degeneracy of the genetic code.

The percentage similarity is determined by comparing a given sequence with the reference sequence. When they have different lengths, the percentage similarity is based on the percentage of nucleotides in the shortest sequence which are similar to those in the longest sequence.

The degree of similarity can be conventionally determined using software such as ClustalW (Thompson et al, Nucleic Acid Research (1994), 22: 4673-4680) distributed by Julie Thompson (Thompson@EMBL-Heidelberg.de) and Toby Gibson (Gibson@EMBL-Heidelberg.de) at the European Molecular Biology Laboratory, Meyerhofstrasse 1, D-69117, Heidelberg, Germany. ClustalW can also be downloaded from a number of websites including IGBMC (Institut de Génétique et de Biologie Moléculaire et Cellulaire, B P 163, 67404 Illkirch Cedex, France; ftp://ftp-igbmc.u-strabg.fr/pub/) and EBI (ftp://ftp.ebi/ac.uk/pub/software/) and all sites linking to the Bioinformatics Institute (Wellcome Trust Genome Campus, Hinxton, Cambridge, CB10 1SD, UK).

The isolated nucleic acids of the invention can in particular comprise other sequences intended to improve the expression and/or activity of the enzyme produced.

As an example, they can be:

sequences encoding a signal sequence for their secretion;

duplication of the sequence encoding the CD2 catalytic domain.

Preferably, an isolated nucleic acid of the invention comprises:

a) two sequences encoding catalytic domains having at least 50%, preferably at least 80% similarity with SEQ ID No: 3;

b) a sequence enclosing the glucan binding domain, the latter preferably being located between the two sequences in a).

A nucleic acid of the invention can also comprise:
a promoter suitable for its expression in a selected host cell;
a sequence encoding a signal peptide; and/or
one or more variable sequences;
said sequence or sequences all being located in the 5' portion of sequences encoding the catalytic domain(s).

A more particular example of an isolated nucleic acid of the invention comprises:
a) SEQ ID No: 4;
b) a sequence having at least 80% similarity with SEQ ID No: 4; or
c) the complementary strand to sequence a) or b); or
d) a sequence hybridizing a), b) or c).

The hybridization in d) is carried out under standard conditions, and preferably under stringent conditions. The term "hybridization under stringent conditions" means that there is at least 80% sequence identity with the sequence which is to be hybridized, preferably an identity of at least 90% of the sequence which is to be hybridized, under conditions which are, for example, described in Sambrook and Russel ($3^{rd}$ edition, 2001, Cold Spring Harbor Laboratory Press, Cold Spring Harbor, N.Y.).

The invention also concerns a gene encoding a dextransucrase that can form at least 15% $\alpha(1\rightarrow 2)$ linkages. In addition to the encoding sequence, the gene comprises sequences that allow transcription initiation and sequences that allow attachment of messenger RNA to the ribosome (RBS). SEQ ID No: 5 represents a gene structure as isolated from *L. mesenteroides* NRRL B-1299.

The nucleotides upstream of the translation initiation ATG are numbered 1 to 232.

The existence of a RBS sequence can be identified between nucleotides 218 and 223 as well as the consensus sequences −35 and −10 located between nucleotides 82 and 86 (TTGAA) on the one hand and 100 and 105 (ATAAAT) on the other hand.

Any nucleic acid sequence that can be hybridized with DNA of SEQ ID No: 4 or its complementary strand is capable of encoding an enzyme having the properties and characteristics of the enzyme of the invention. This applies to natural sequences existing in micro-organisms other than *L. mesenteroides* NRRL B-1299 and isolated from gene libraries of micro-organisms, and to those prepared by genetic engineering or by chemical synthesis.

In particular, the sequences upstream of the translation initiation ATG and necessary for expression of the protein can advantageously be substituted by transcription initiation and/or ribosome binding sequences suitable for the expression system selected for the coding sequence.

A nucleic acid sequence that is capable of hybridizing under stringent conditions with the isolated nucleic acid of the invention also comprises fragments, derivatives or allele variations of the nucleic acid sequence of the invention which encodes a protein having the enzymatic activity described above. Thus, the fragments are defined as fragments of nucleic acid molecules that are sufficiently long to encode a protein that has conserved its enzymatic activity. This also encompasses fragments that are free of the sequence encoding the signal peptide responsible for protein secretion.

The term "derivative" means a sequence that is different from the original sequence in one or more positions but which has a high degree of similarity with said sequences. In this context, "similarity" means at least 80% identity of the nucleotides, preferably at least 90% identity with the original sequence. The modifications in this case are deletions, substitutions, insertions or recombinations provided that the enzyme encoded by these homologous sequences has the enzymatic activity of the polypeptides of the invention.

The nucleic acid sequences of the invention as described above and qualified by derivatives of said molecules as defined above are generally variations exerting the same biological function. Said variations can be natural variations, in particular those observed from one species to another and resulting in interspecies variability or, in contrast, those introduced via directed or random mutagenesis or by DNA shuffling.

Similarly, the invention encompasses isolated nucleic acids encoding a glycosyltransferase that can catalyze the synthesis of dextran or oligosaccharide carrying at least 20% and preferably at least 30% type $\alpha(1\rightarrow 2)$ linkages obtained by DNA shuffling and comprising:
a step for random modification of one of the sequences defined above and in particular SEQ ID Nos: 3 and 4 and establishing the variations;
a step for expressing a host housing a variation from said modified sequences in a suitable host cell;
a step for screening hosts expressing an enzyme that can form more than 20% and preferably more than 30% $\alpha(1\rightarrow 2)$ bonds on a suitable substrate and a step for isolating the improved gene or genes.

An isolated nucleic acid of the invention can also comprise:
a) a sequence containing at least 80% similarity with the sequence encoding a dextransucrase expressed by the plasmid pCR-T7-dsrE in *E. coli* deposited at the CNCM on $15^{th}$ Mar. 2001 with accession number I-2649 (*E. coli* JM 109 [pCR-T7-dsrD]), or
b) a complementary sequence of the sequence in a).

The denomination of the strain transformed by the recombinant plasmid pCR-T7-dsrE deposited at the CNCM is that indicated above in brackets. This does not affect the change in the denomination of the gene carried out following deposition of said strain for the reasons given above.

The invention also concerns nucleic acid fragments as defined above, which are hybridizable with SEQ ID No: 4 and can be used as hybridization probes for detecting sequences encoding the enzymes of the invention. Said fragments can be prepared using any technique known to the skilled person.

In addition to hybridization probes, amplification primers also form part of the invention. Said primers are fragments which are hybridizable with SEQ ID No: 4 or with its complementary strand and which allow amplification of specific sequences encoding dextransucrases present in a prokaryotic or eukaryotic animal or plant organism.

The use of said amplification primers allows the use of a method for identifying the possible existence of a gene encoding an enzyme that can catalyze synthesis of GOS with $\alpha(1\rightarrow 2)$ linkages in said organism, said method also forming part of the invention.

The invention also concerns expression vectors comprising a nucleic acid as described above under the control of a sequence allowing its expression and preferably its excretion in prokaryotic or eukaryotic cells. The term "prokaryotic cells" preferably denotes bacteria selected from a group comprising *E. coli, Lactococcus, Bacillus* and *Leuconostoc*. The term "eukaryotic cells" preferably means eukaryotes selected from a group containing yeasts, fungi and plants.

The vector comprises a promoter suitable for expression of the isolated nucleic acid of the invention in the selected expression system. As an example, the T7 bacteriophage promoter could advantageously be selected for expression in *E. coli*.

The invention also concerns host cells, prokaryotic or eukaryotic, transformed by a nucleic acid of the invention, preferably comprised in an expression vector carrying a promoter, adapted for expression in the selected host cells. The transformed cells are selected from Gram– bacteria such as *E. coli*, or from Gram+ bacteria such as *Lactococcus, Bacillus, Leuconostoc*, or from eukaryotes in a group comprising yeasts, fungi and plants.

One particular example of a cell transformed in accordance with the invention is the *E. coli* strain harboring a plasmid termed pCR-T7-dsrE carrying the SEQ ID No: 4 under the control of the T7 bacteriophage promoter deposited at the CNCM on 15$^{th}$ Mar. 2001 under accession number I-2649.

The present invention also concerns a method for producing a glycosyltransferase that can form dextrans or oligosides having at least 15% and preferably at least 20% of type α(1→2) osidic linkages and comprising:
   a) inserting a nucleic acid or a vector as defined above into a host cell that can express and preferably secrete the glycosyltransferase;
   b) characterizing the enzymatic activity being investigated using any of the methods accessible to the skilled person;
   c) purifying the enzyme from a cell extract.

The term "method for characterizing enzymatic activity known to the skilled person" means the methods described in the literature, for example in reference (2), and novel methods that may be developed to allow identification and discrimination of glucooligosaccharides having the desired degree of linkages.

In fact, it concerns any screening method that can identify the presence of α(1→2) linkages in a GOS.
Examples are:
HPLC in which GOS migration varies as a function of the nature and position of the linkages, in particular those containing the α(1→2) bond at the reducing end and those containing this bond on the penultimate glucose; and/or
nuclear magnetic resonance (NMR);
the existence of a positive reaction with specific monoclonal antibodies of α(1→2) bonds on the reducing end and/or specific monoclonal antibodies of α(1→2) bonds on the penultimate glucose of the GOS.

The invention also concerns a method for obtaining a glycosyltransferase that can have oligosides or dextrans having a percentage of α(1→2) linkages of more than 15% and preferably more than 30% of the totality of the osidic bonds and comprising a step for modifying SEQ ID No: 4 by addition, deletion or mutation provided that:
   the reading frame is not modified; and
   the following amino acids are conserved after translation:
      W in positions 425 or 2122, encoded by the TGG triplet in positions 1273 and 6364;
      E in positions 430, 565, 2127 and 2248, encoded by GAA triplets in positions 1288, 1693, 6379 and 6742 respectively;
      D in positions 487, 489, 527, 638, 2170 and 2210, encoded by GAT triplets in positions 1459, 1465, 1579, 1912, 6508 and 6628 respectively;
      D in positions 2172 and 2322 encoded by GAT triplets in positions 6514 and 6964;
      H in position 637 and 2321, respectively encoded by the CAT triplet in position 1909 and CAC in position 6961;
      Q in positions 1019 and 2694, respectively encoded by triplets CAA (position 3055) and CAG (position 8080).

A method for producing a glycosyltransferase according to the invention having the same characteristics as above can also comprise:

a step for randomly modifying SEQ ID No: 4 and establishing a library of variations;
a step for expressing a host housing a variation from said modified sequences in a suitable host cell;
a step for screening hosts expressing an enzyme that can form more than 15% and preferably more than 30% of α(1→2) bonds on a suitable substrate;
and a step for isolating the improved gene or genes.

In a further implementation of the invention, the method consists of modifying SEQ ID No: 3 by duplicating all or part of the CD2 catalytic domain.

It should be understood that the methods above are not only aimed at obtaining a glycosyltransferase that can form oligosides having a constant and reproducible percentage of α(1→2) linkages of more than 15% of the total linkages, but also to improve the degree of α(1→2) linkages with the aim of modifying the properties of the oligosides obtained to improve their dietetic properties or their capacity to maintain or re-establish bacterial flora associated with certain organs of the human or animal body.

Finally, the present invention concerns glycosyltransferases that can be obtained by a method as defined above and which can form at least 15% and preferably at least 30% of type α(1→2) osidic linkages in glucooligosaccharides.

Finally, the invention pertains to the use of glycosyltransferases of the invention as well as those that can be obtained by the methods mentioned above, in the production of a composition with a pre-biotic effect or in the manufacture of a dermatological, cosmetic or pharmaceutical composition.

Non-limiting examples that can be cited are the improvement in intestinal transit in animals and in man, an improvement in calcium and/or magnesium assimilation and of minerals in general, preventing cancer of the colon and prevention or treatment of skin affections such as acne, dandruff or body odor.

The advantage of the polypeptides and nucleic acids encoding said polypeptides of the invention is not only in improvements in terms of quality, yield, reproducibility and cost of glycosyltransferases that can form oligosaccharides with type α(1→2) osidic linkages, but also in producing novel enzymes the functionality of which is improved.

The figures, examples and detailed description below provide non-limiting illustrations of the particular characteristics and functionalities of polypeptides with enzymatic activity and sequences encoding them. In particular, they can illustrate more precisely the specificity of the catalytic domain present in the carboxylic portion of the enzyme of the invention and its potential evolution to obtain improved enzymes.

KEY TO FIGURES

FIG. 1: Structure of native glycosyltransferases and derived recombinant proteins: FIG. 1*a*) shows the structure of glycosyltransferases and dextransucrases described in the literature (1). PS: signal peptide; ZV: variable zone; CD: catalytic domain; GBD: glucan binding domain. FIG. 1*b*) shows the structure of the glycosyltransferase of the invention. FIGS. 1*c*) to 1*i*) show different constructions comprising deletions in comparison with native DSR-E protein. Δ(PS) corresponds to the control constituted by the entire form cloned into the pBAD-TOPO thiofusion system (Invitrogen).

Figures 2, 3:
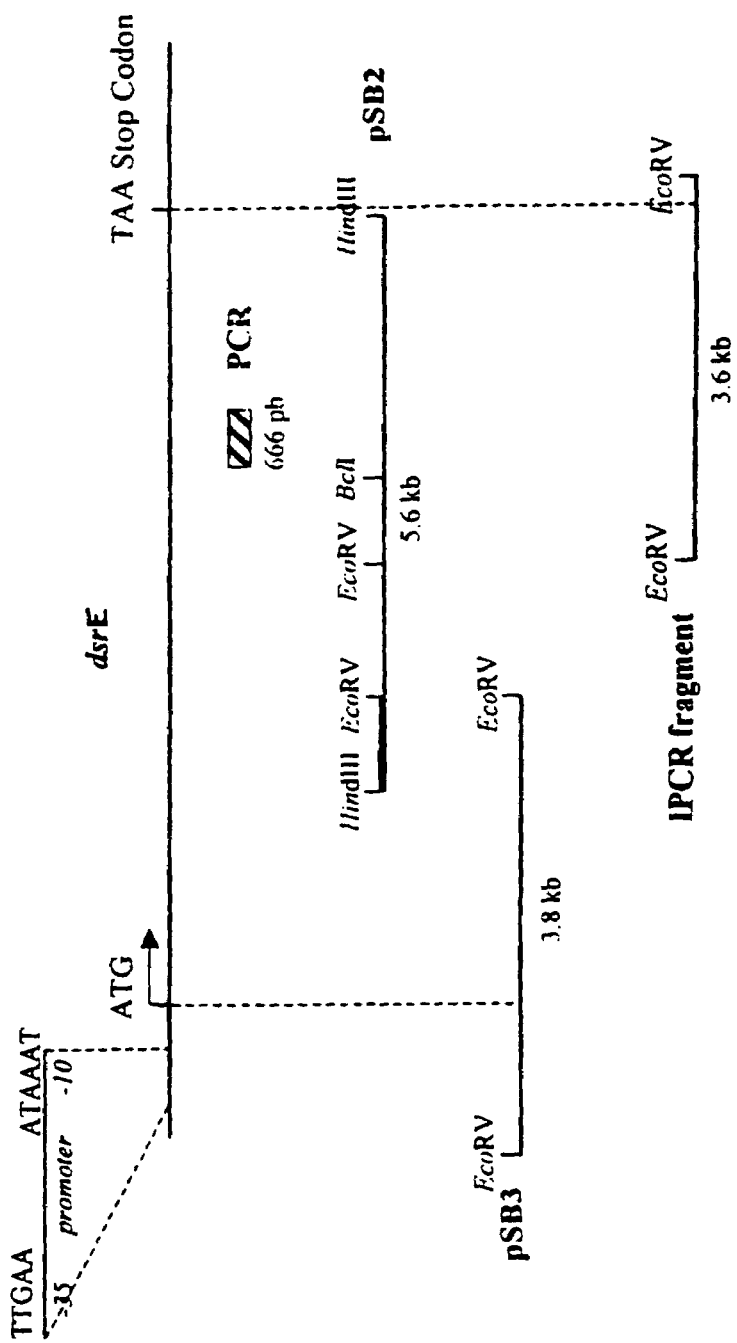

FIG. 2: Diagrammatic summary of the method for cloning the nucleotide sequence encoding a glycosyltransferase of the invention using a genome library by using a PCR probe described in Table I and a HindIII/EcoRV probe respectively.

FIG. 3: Comparison of the signal sequences of different glycosyltransferases of *L. mesenteroides* (residues 1-40 of SEQ ID NO: 2). The conserved amino acids are shown in bold. DSR-B: *L. mesenteroides* NRRLB-1299 (4) (SEQ ID NO: 45); DSR-S: *L. mesenteroides* NRRLB-512F(5) (SEQ ID NO: 46); ASR: *L. mesenteroides* NRRL B-1355 (6) (SEQ ID NO: 47).

FIG. 4: Alignment of 11 repeat sequences (SEQ ID NOS: 50-61) of the DSR-E enzyme and observed in the variable zone.

FIG. 5: Alignment of conserved sequences in the catalytic domain (SEQ ID NOS: 6-17 and 62-103

Block A: essential amino acids of the N-terminal portion of the catalytic domain;

Block B: amino acids of the catalytic saccharose binding domain;

Blocks C, D, E: blocks containing three amino acid residues involved in the catalytic triad (6);

Block F: sequence containing glutamine 937 of GTF-1 studied by Monchois et al (7).

The entirely conserved amino acids are indicated in bold. "*": conservative substitutions; ":": semi-conservative substitutions; - - - : gap. The numbering is that for SEQ ID No: 2.

Figure 6:
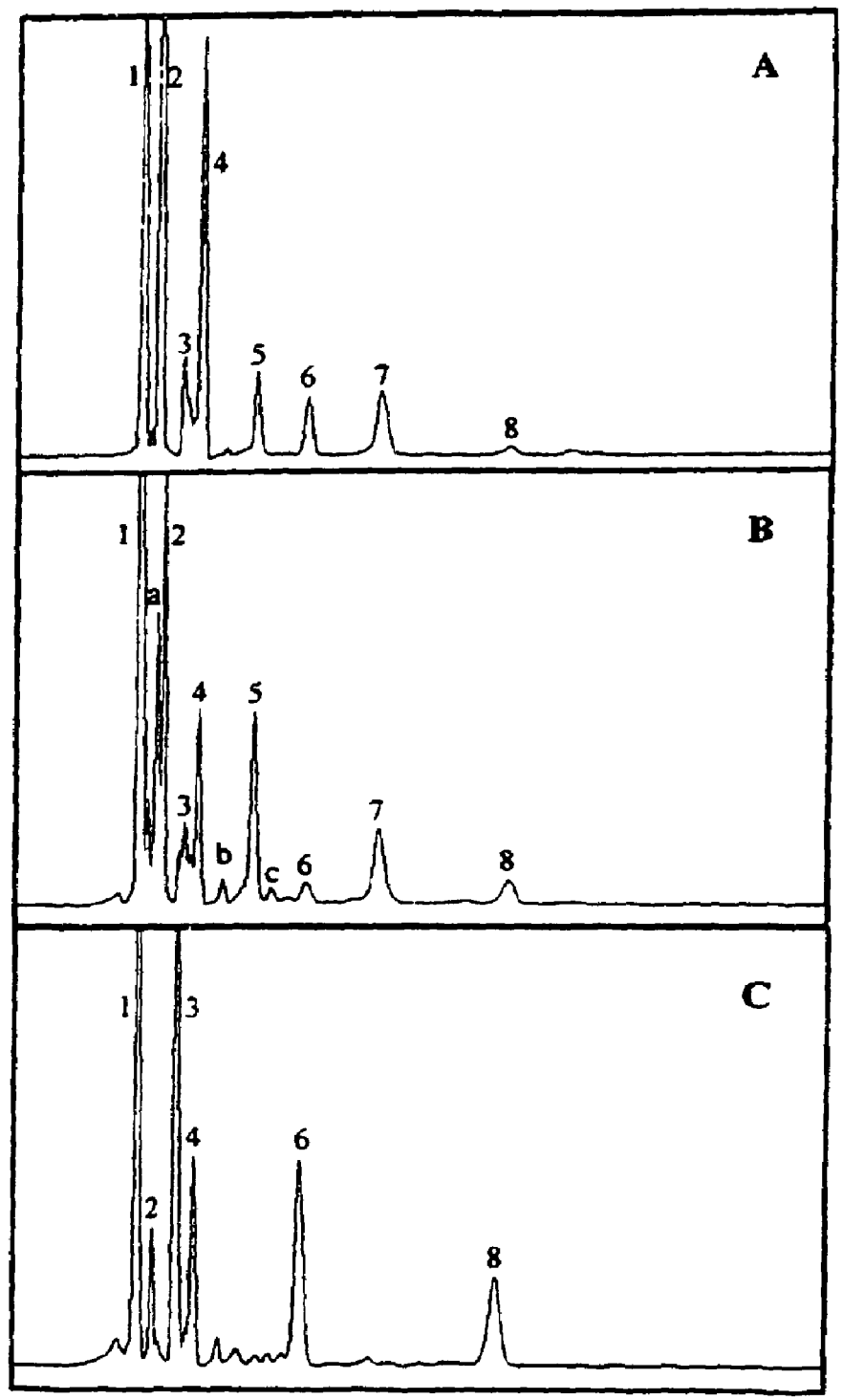

FIG. 6: HPLC characterization of products synthesized by recombinant enzyme DSR-E.

6A: HPLC analysis of glucooligosaccharides obtained with dextransucrases of *L. mesenteroides* NRRL B-1299.

6B: HPLC analysis of glucooligosaccharides obtained by recombinant DSR-E. The following peaks are identified:
1: fructose
2: maltose;
3: sucrose;
4: panose;
5: R4;
6: OD4;
7: R5;
8: OD5;
A, B, C: unidentified peaks.

6C: recombinant DSR-E deleted from the catalytic domain of the carboxylic portion of the enzyme (ΔDSR-E).

Figure 7:
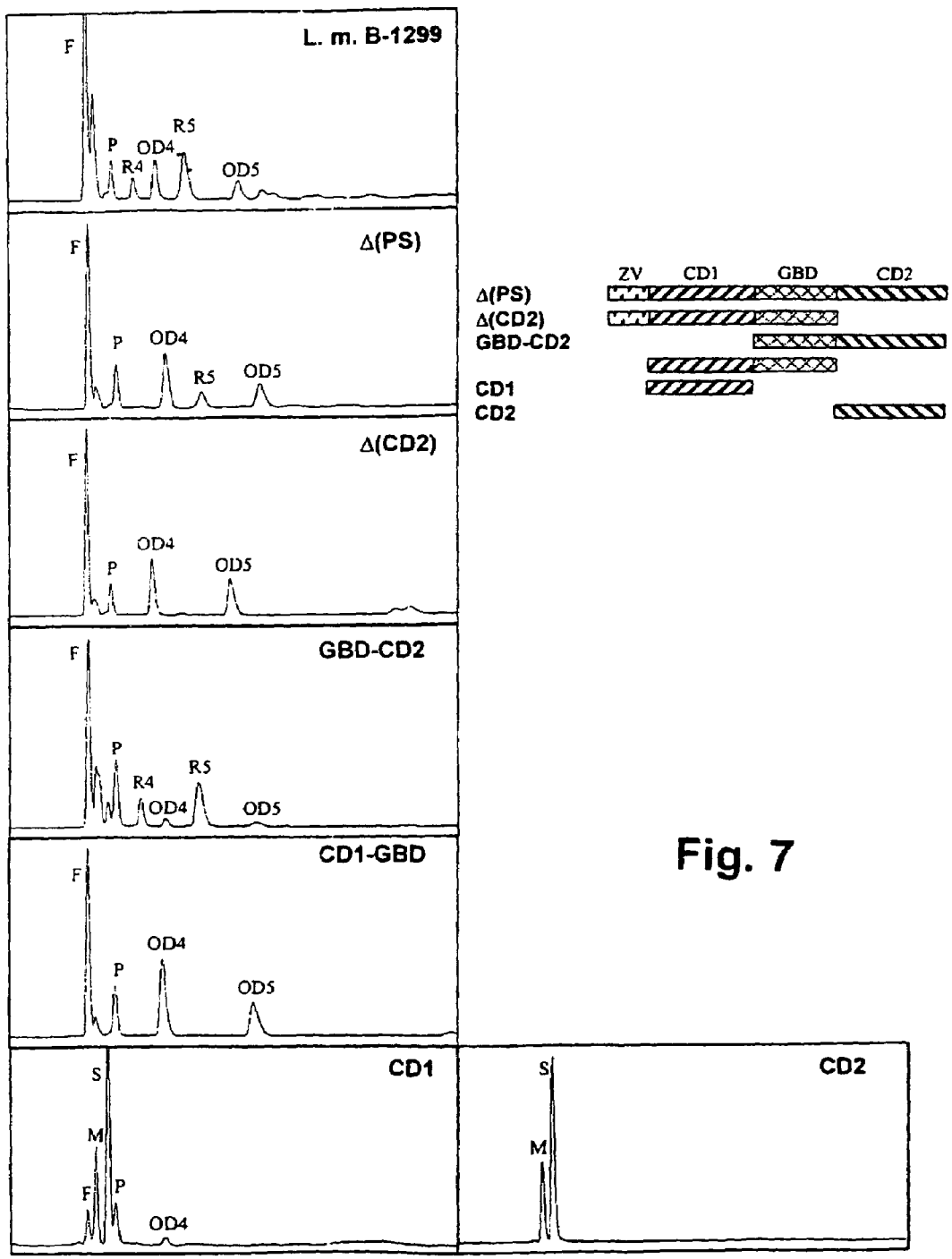

FIG. 7: HPLC analysis of acceptor on maltose reaction products synthesized by different entire forms and deleted from the DSR-E protein.

L.m. B-1299: mixture of dextransucrases produced by *L. mesenteroides* NRRL B-1299.

The peaks were identified as follows:
F: fructose;
M: maltose;
S: saccharose
P: panose;
R4, R5: GOS comprising α(1→2) bonds;
OD4, OD5: GOS free of α(1→2) bonds.

MATERIALS AND METHODS

1) Bacterial Strains, Plasmids and Growth Conditions:

All strains were kept at −80° C. in tubes containing 15% glycerol (v/v).

*Leuconostoc mesenteroides* B-1299 (NRRL, Peoria, USA) was cultivated at 27° C. with stirring (200 rpm) on standard medium (saccharose 40 g/l, potassium phosphate 20 g/l, yeast extract 20 g/l, MgSO$_4$,7H$_2$O 0.2 g/l, MnSO$_4$,H$_2$O 0.01 g/l, NaCl 0.01 g/l, CaCl$_2$ 0.02 g/l, FeSO$_4$,7H$_2$O 0.01 g/l), the pH being adjusted to 6.9.

*Escherichia coli* DH5α and JM109 were cultivated on LB medium (Luria-Bertani).

Selection of pUC18 or pGEM-T Easy recombinant clones was carried out on LB-agar dishes supplemented with 100 μg/ml of ampicillin, 0.5 mM of isopropyl-β-D-thiogalactopyranoside (IPTG) and 40 μg/ml of 5-bromo-4-chloro-3-indolyl-β-D-galactopyranoside (X-gal). *E. coli* TOP 10 cells were used to clone the PCR TOPO Cloning (Invitrogen) product and cultivated on LB medium supplemented with kanamycin in a concentration of 50 μg/ml.

Regarding expression of dsrE, the ECHO Cloning System cloning kit (Invitrogen) allows a PCR product to be cloned in a donor vector (pUNI/V5-His-TOPO), preceding a step for recombination with a suitable acceptor vector (pCR-T7-E). This system requires *E. coli* PYR1, TOP 10 and PL21(DE3) pLysS cells cultivated on LB medium supplemented with 50 μg/ml of kanamycin as well as 34 μg/ml of chloramphenicol for the BL21(DE3)pLysS strain.

Digested and dephosphorylated pUC18 plasmids from Pharmacia (Amersham Pharmacia Biotech) were used to constitute the genomic DNA library of *L. mesenteroides* NRRL B-1299. Cloning of the PCR product necessitated the use of the pGEM-T Easy plasmid (Promega) and TOPO-XL plasmid (Invitrogen) for fragments of more than 2 kbp.

The pBAD-TOPO Thiofusion system (Invitrogen) used to construct the different deleted forms of the DSR-E protein used the araBAD promoter the control mechanisms for which involve the AraC regulatory protein. In the absence of an inducer, namely L-arabinose, the dimeric AraC protein associates with the regulatory structures of the operon and entrains the formation of a DNA loop, said loop then blocking transcription of genes placed under the control of the araBAD promoter. In the presence of L-arabinose, in contrast, AraC forms a complex which liberates the DNA loop and allows transcription initiation. The base expression can be limited by adding glucose to the culture medium: this reduces the level of cyclic AMP and thus concomitant activation of the CAP protein (cAMP activator protein). The level of activation obtained is a function of the concentration of L-arabinose so that the optimum conditions for production of the protein of interest can be selected with accuracy.

Further, the use of this vector can allow a 12 kDa thioredoxin tag to be positioned on the N-terminal end of the protein of interest. This fusion encourages the translation of the gene encoding said protein of interest. The tag protein can also enhance the solubility of the protein to which it is fused. The pBAD-TOPO Thiofusion system is designed to allow ready elimination of the thioredoxin tag by simple cleavage using enterokinase. Finally, using this expression system, a histidine tag is inserted on the C-terminal end side of the protein of interest. Such a tag is used to purify said protein by affinity.

Within the context of using this system, the *E. coli* TOP 10 strain was cultivated on LB medium supplemented with 100 μg/ml of ampicillin.

2) Gel Electrophoresis, Location and Characterization of Enzyme:

After culturing *L. mesenteroides* NRRL B-1299 for 7 h, the medium was centrifuged (7000 rpm, 4° C., 30 min) and the cells, in which 90% of the enzymatic activity was found, were concentrated 10 times in an acetate buffer solution (20 mM, pH 5.4), heated for 5 minutes at 95° C. in the presence of denaturing solution (tris HCl 62.5 mM, SDS 4%, urea 6M, bromophenol blue 0.01% and β-mercaptoethanol 200 mM). 300 μl of the mixture was deposited on 7% polyacrylamide gel. After migration, the total proteins were revealed by amido black staining, while the dextransucrase activity was detected by staining with Schiff's reagent polymer after synthesizing the dextran in situ. The bands corresponding to the active dextransucrases were excised and incubated separately in 2 ml of 20 mM sodium acetate solution, pH 5.4, containing 100 g/l of saccharose and 50 g/l of maltose. After total consumption of saccharose, the reaction was stopped by heating to 95° C. for 5 minutes, and the reaction medium was centrifuged for 5 minutes at 15000 g to eliminate the insoluble dextran. The samples were analyzed by reverse phase chromatography (C18 column, Ultrasep 100, 6 μm, 5×300 mm, Bishoff Chromatography) using ultrapure water as the eluent, at a constant flow rate of 0.5 ml/min. The oligosaccharides were separated for 30 minutes at ambient temperature and detected by refractometry. Peptide sequencing was carried out on the selected protein bands by the Laboratoire de Microséquençage, Institut Pasteur, Paris.

3) Molecular Biological Techniques Used

Purification of the *E. coli* plasmid and purification of the genomic DNA of *L. mesenteroides* was carried out using the QiaPrep Spin Plasmid kit and the Cell Culture DNA maxi kit (Qiagen) respectively. The amplification and cloning methods were carried out using standard techniques (Sambrook and Russel, 2001, supra). Restriction and modification enzymes from New England Biolabs or Gibco BRL were used in accordance with the manufacturer's instructions.

PCR was carried out with primers selected on the basis of the protein sequence obtained on an isolated band from gel electrophoresis (see supra, gel electrophoresis and enzyme localization). Two peptides were selected:

29-FYFESGK (SEQ ID NO: 18); and
24-FESQNNNP (SEQ ID NO: 19)

and used to synthesis degenerate oligonucleotides indicated in Table I below.

In this table, the numbering of which follows that of SEQ ID No: 4, it appears that the presence of a serine residue in the two peptides necessitates the synthesis of two primers for each peptide since serine can be encoded by six different codons. ECHO-dir and ECHO-inv are primers which allowed amplification of dsrE by PCR for cloning into the ECHO Cloning (Invitrogen) expression system.

PCR

PCR was carried out using a Perkin-Elmer thermocycler, model 2400, with 50 nanograms of genomic DNA. The quantities of primers used was 10 μM of 29-Dir-1 and of 24-Inv1. 250 μM of each triphosphate deoxynucleotide and Taq polymerase were added to the reaction mixture.

After amplification of 25 cycles at 94° C. for 30 seconds then at 50° C. for 30 seconds, then at 72° C. for 5 minutes, a 666 base pair fragment was obtained.

Certain fragments were amplified using the "Expand Long Template PCR" (Roche Boehringer Mannheim) system, in accordance with the manufacturer's instructions. This system can amplify large fragments of up to about 20 kbp highly effectively. The combination of two DNA polymerases can minimize errors during the elongation phases.

Southern Hybridization and Gene Library of *L. mesenteroides* NRRL B-1299

Chromosomal DNA from *L. mesenteroides* NRRL B-1299 was digested with different restriction enzymes then separated by electrophoresis on 0.8% agarose gel in TAE 0.5× buffer.

Genomic libraries of the bacteria were transferred onto nylon hybond N+ membranes (Amersham PharmiciaBiotech). Hybridization was carried out using the 666 base pair fragment of deoxy-adenosine-triphosphate labeled with $^{32}$P. The labeling reaction was carried out using the "Mega Prime DNA Labelling System Kit" (Amersham PharmaciaBiotech) labeling kit, followed by purification of the probe on MicroSpin S-200HR columns. Pre-hybridization and hybridization was carried out under highly stringent conditions (65° C. overnight using the normal methods) (Sambrook and Russel, 2001, supra).

Reverse PCR

The reverse PCR reaction produces a linear DNA fragment from a circular matrix using divergent primers.

TABLE 1

SEQ ID NOS: 18-27

| Designation | Description | Sequence 5'-3' |
|---|---|---|
| 29-dir1 | FYFESGK | TT(C/T)TA(C/T)TT(C/T)GA(A/G)TCAGG(C/G)AA(A/G) |
| 29-dir2 |  | TT(C/T)TA(C/T)TT(C/T)GA(A/G)AGCGG(C/G)AA(A/G) |
| 24-inv1 | FESQNNNP | (T/G)GG(G/A)TT(G/A)TT(G/A)TTTTGTGA(T/C)TCAAA |
| 24-inv2 |  | (T/G)GG(G/A)TT(G/A)TT(G/A)TTTTGGCT(T/C)TCAAA |
| IPCR-rev | sequence nt 5769-5798 | CCCTTTACAAGCTGATTTTGCTTATCTGCG |
| IPCR-dir | sequence nt 8311-8342 | GGGTCAAATCCTTACTATACATTGTCACACGG |
| ECHO-dir | sequence nt- 6-39 | AGTTGTATGAGAGACATGAGGGTAATTTGTGACCGTAAAAATTG |
| ECHO-inv | sequence nt 8457-8504 | ATTTGAGGTAATGTTGATTTATCACCAT-CAAGCTTGAAATATTGACC |

Genomic DNA from *L. mesenteroides* NRRL B-1299 was digested with EcoRV under the conditions recommended by the manufacturer.

After re-circularization, the digestion products were used as a matrix in a reverse PCR reaction [Extrapol II DNA polymerase (Eurobio), reaction volume of 50 µl, reverse PCR reaction parameters: 25 cycles; 94° C.; 30 seconds; 51° C., 30 seconds; 72° C., 3 minutes]. The two primers were selected as a function of the pSB2 insert sequence as indicated in FIG. 2.

FIG. 2 summarizes the conditions for obtaining different plasmids carrying dsrE fragments by screening the gene library and using the probes described above.

DNA Sequence and Analysis

After sequencing the peptides, degenerate primers marked out because of the frequency of use of codons in the dextransucrase genes of *L. mesenteroides* NRRL B-1299 were synthesized and allowed amplification of a 666 bp fragment. Sequencing this fragment revealed strong homologies with the genes of known dextransucrases, even though it was entirely novel.

The use of this fragment as a homologous probe in Southern experiments allowed positive signals on different tracks of genomic DNA to be marked. A first HindIII library was then screened and a recombinant plasmid termed pSB2 containing a 5.6 kbp insert was purified. An analysis of the sequence for this HindIII fragment revealed an open reading frame covering the whole insert. Then a EcoRV library was screened with a HindIII/EcoRV probe isolated at the N-terminal end of the 5.6 kbp HindIII insert. A recombinant pSB3 recombinant plasmid, tested positively by dot-blot, was shown to contain a 3.8 kbp insert which, after sequencing, was shown to contain the initiation codon for translation and the promoter region of the novel dextransucrase gene termed dsrE.

With the aim of obtaining the dsrE termination codon, reverse PCR was carried out on genomic DNA from *L. mesenteroides* NRRL B-1299 digested with EcoRV and re-ligated to itself, using divergent oligonucleotide primers designated from the pSB2 insert sequence. A single fragment with the expected size of 1 kbp was amplified then cloned in pGEM-T Easy to obtain the pSB4 plasmid. After sequencing, the amplified sequence located downstream of the HindIII site comprised 221 bp and contained the reading frame termination codon for dsrE located 30 bp downstream of the HindIII restriction site.

Sequencing of the different fragments carried by the three plasmids was carried out on both strands by the company Genome Express. Sequence analyses of the nucleotides was carried out using "ORF Finder" (http://www.ncbi.nlm.nih.gov/gorf/gorf.html), Blast (http://www.ncbi.nlm.nih.gov/blast/blast.cqi, Altschul et al, 1997), ClustalW (http://www2.ebi.ac.uk/clustalw, Thompson et al, 1994), PRODOM (http://protein/tolulouse.inra.fr/prodom.html, Corpet et al, 2000), PFAM (http://pfam.wustl.edu.hmmsearch.shtml, Bateman et al, 2000) and SAPS (http://bioweb.pasteur.fr/segana/interfaces/saps.html, Brendel et al, 1992), all of this software being available on the Internet.

Protein Expression

Two cloning and expression systems were used to produce recombinant proteins in *E. coli*, namely the ECHO-Cloning and pBAD-TOPO Thiofusion (Invitrogen) systems.

By way of example, the method for cloning the nucleotide sequence encoding the DSR-E protein using the ECHO-Cloning system will now be briefly described.

Two primers as proposed in Table I above were used for amplification using the "Expand Long Template" system under the following conditions: 94° C. for 3 minutes, followed by 25 cycles at 94° C. for 30 seconds, 55° C. for 30 seconds, and 68° C. for 7 minutes. The PCR products were then cloned into the pUNI/V5-His-TOPO vector to obtain a donor vector (pUNI-dsrE) to be recombined with an acceptor vector (pCR-T7-E) and adapted for expression in *E. coli*. The final plasmid was designated pCR-T7-dsrE.

This construction, placing the dsrE gene under the control of the bacteriophage promoter T7, allowed inducible expression of the dsrE gene.

After induction with 1 mM of IPTG, the transformed *E. coli* BL21 cells were harvested by centrifuging after 4 hours growth and re-suspending at a final optical density of 80 at 600 nm in a 20 mM sodium acetate buffer, pH 5.4, and 1% Triton X100 (v/v) in the presence of 1 mM of PMSF to prevent proteolysis in the cell extracts after sonication.

Similar experiments carried out with the pBAD-TOPO Thiofusion system allowed the recombinant vector pBAD-TOPO-dsrE to be constructed.

Enzymatic Tests

The enzymatic reactions were carried out under standard conditions at 30° C. in a 20 mM sodium acetate buffer, pH 5.4, $NaN_3$ 1 g/l and saccharose, 100 g/l. The activity of the DSR-E enzyme was determined by measuring the rate at which the reducing sugars were liberated, represented here by fructose, using the dinitrosalicylic acid method which is well known to the skilled person. One unit is defined as the quantity of enzyme which would catalyze the formation of 1 µmol of fructose per minute under standard conditions. The oligosaccharides were synthesized in a reaction medium containing 100 g/l of maltose, 200 g/l of saccharose and 0.5 units/ml of DSR-E.

As for the dextran synthesis, the enzymatic reaction was continued for 24 hours in the presence of 100 g/l of glucose. The dextran produced was precipitated in the presence of 50% (v/v) ethanol and washed twice in 50% ethanol (v/v) prior to freeze drying. It was then dissolved in an amount of 10 mg/ml in $D_2O$ and analyzed by $^{13}C$ NMR spectrometry.

HPLC Separation

100 µl samples were removed and heated at 95° C. for 5 minutes then diluted in ultrapure water to obtain a final concentration of total sugars of less than 5 g/l. After centrifuging, the residual substrates and the different species formed were analyzed by HPLC on a C18 column (Ultrasep 100, 6 µm, 5×300 mm, Bishoff Chromatography).

The oligosides were separated at ambient temperature for 30 minutes in ultrapure water used as the eluent, at a flow rate of 0.5 ml/min. Detection was accompanied by refractometry.

These conditions allowed the following species to be separated: fructose, maltose, leucrose, saccharose, and oligosides with a degree of polymerization that did not exceed 6.

Calculation of Yields

The method for calculating the yields for the oligoside synthesis reactions took into account the residual concentration of the acceptor in accordance with the following formula:

$$R = \{[GOS\ final] - [initial\ GOS]\} / \{0.474 \times [sacchraose\ consumed] + [acceptor\ consumed]\}$$

in which R represents the real yield of the total GOS synthesis reaction, the concentrations being expressed in g/l.

Construction of Different Deleted Forms of DSR-E Protein

The different deleted forms of the DSR-E protein [FIG. 1*c*) to 1*i*)] were obtained by PCR amplification of fragments corresponding to the dsrE gene then cloning in the pBAD-TOPO Thiofusion vector described above. The primers used for amplification of the regions selected from the dsrE gene are shown in Table II below. The positions of the primers are shown with respect to SEQ ID No: 5, relating to the sequence for the dsrE gene. The bases mutated to introduce the NcoI restriction site are shown in bold and the resulting NcoI site is underlined.

TABLE 2

SEQ ID NOS: 28-34

| Designation | Positions | Sequence 5'-3' |
|---|---|---|
| pBAD-PS/ ZV-dir | 344-373 | G<u>CCATGG</u>CAAATACGATTGCAGTTGACACG |
| pBAD-ZV/ CD1-dir | 971-1001 | G<u>CCATGG</u>ACGGTAAAACCTATTTTCTTGACG |
| pBAD-CD1/ GBD-dir | 3656-3682 | T<u>CCATGG</u>GTGAAAAAACAAGCACCGGC |
| pBAD-GBD/ CD2-dir | 6167-6189 | A<u>CCATGG</u>ATATGTCTACTAATGC |
| pBAD-CD1/ GBD-inv | 3638-3658 | TAACTGTTTAGGCAAGAATCC |
| pBAD-GBD/ CD2-inv | 6146-6172 | TAATGTATTAGTGAATAAGTATTCACC |
| pBAD-ent-inv | 8714-8737 | AATTTGAGGTAATGTTGATTTATC |

The above direct and reverse primers were designed to ensure translational fusion of the N-terminal thioredoxin tag and the C-terminal polyhistidine tag of the truncated protein forms, satisfying the open reading frames for the regions encoding said forms.

If the pBAD-TOPO Thiofusion plasmid contains a specific restriction site for the NcoI enzyme located at the 5' end of the region encoding thioredoxin, a second NcoI site is introduced into each direct primer to enable extraction of that region if required.

The PCR amplification reactions were carried out using the "Expand Long Template" system under the following conditions: pre-denaturing at 94° C. for 3 minutes followed by 25 cycles at 94° C. for 30 seconds, 52° C. for 30 seconds and 68° C. for 7 minutes.

The amplification products generated were then cloned into the pBAD-TOPO Thiofusion vector for subsequent transformation of the *E. coli* TOP 10 strain. Recombinant clones were selected, their restriction profile analyzed to identify a recombinant plasmid carrying the insertion orientated as expected for each of the investigated forms.

EXAMPLE 1

Characterization and Purification of the DSR-E Enzyme and Obtaining the dsrE Gene The enzymes produced by *L. mesenteroides* cultures and obtained on a polyacrylamide gel in SDS as described in the Materials and Methods section were isolated by cutting the gel.

The GOSs produced by the isolated enzymes were analyzed by HPLC using the methods described in (1). The enzyme the activity of which was being investigated was deduced from the nature of the GOSs produced. After trypsic proteolysis and separation of the peptides produced by HPLC, 2 peptides: 29-FYFESGK (SEQ ID NO: 18) and 24-FESQNNNP (SEQ ID NO: 19), were sequenced and used as a model for the synthesis of degenerate nucleotide primers.

The different amplification and cloning steps are shown in FIG. 2. The complete gene was inserted into the pCR-T7-E plasmid and expressed in *E. coli*.

The production of a functional enzyme was attested by the production of GOSs the HPLC analysis of which is shown in FIG. 6*b*).

The size of peaks 5 and 7, representing GOSs with a $\alpha(1\rightarrow2)$ linkage, should in particular be noted.

EXAMPLE 2

Characterization of dsrE and DSR-E Sequences 2.1 Nucleotide Sequence

The nucleotide sequence of the enzyme is shown in SEQ ID No: 4. It is composed of a reading frame of 8506 nucleotides.

The nucleotide sequence for insertion into the pCR-T7-dsrE plasmid contained a ribosome binding site (RBS), 9 bases upstream of the ATG initiation codon and was composed of a hexanucleotide GAGGAA.

2.2 Analysis of Amino Acid Sequence

The 8506 nucleotide dsrE sequence encodes a 2835 amino acid protein shown in SEQ ID No: 2. The isoelectric point for this protein is 4.88 and its theoretical molecular weight is 313.2 kDa. Despite strong similarities with known dextransucrases, DSR-E is characterized by an original structure.

Alignment of the amino acid sequence with known glycosyltransferases and dextransucrases confirmed that the structure in the glycosyltransferase domain and dextransucrases domain was conserved, namely: a signal sequence, a variable zone, a highly conserved catalytic domain and a glucan binding domain. This structure is shown in FIG. 1*a*).

As indicated in FIG. 1*b*), a second catalytic domain forms the carboxy-terminal portion of the enzyme, as confirmed by PRODOM and Blast analysis.

With a molecular weight of 313.2 kDa, DSR-E had about twice the mean molecular weight of other glycosyltransferases and dextransucrases (1), which is in agreement with the presence of a second catalytic domain at the c-terminal end and also with a longer glucan binding region.

a) Analysis of Signal Sequence:

The signal sequence and the nucleotide sequence encoding the peptide signal were highly conserved if compared with other dextransucrases, as shown in FIG. 3. The cleavage site is located between amino acids 40 and 41.

b) Variable Domain:

Downstream of the signal peptide, DSR-E had a 207 amino acid variable domain. When it was compared with other variable glycosyltransferase domains, using a SAPS type alignment program, the presence of a 14 amino acid motif repeated 11 times was revealed, as indicated in FIG. 4.

This alanine-, threonine- and aspartic acid-rich repeat motif has never before been identified.

The role and significance of this region has never been elucidated. Different studies have shown that its deletion does not affect enzymatic activity (4). The role of the 14 amino acid repeat motif, which does not exist in other glycosyltransferases, remains to be determined, however.

c) Analysis of Catalytic Domains:

The first catalytic domain extends from amino acids 248 to 1142 (CD1) of SEQ ID No: 2, while the second is located between amino acids 1980 and 2836 (CD2). These two domains have 45% identity and 65% similarity between them.

CD1 and CD2 contain amino acids already identified in glycosyltransferases and dextransucrases as being essential to their enzymatic activity, as shown in FIG. 5.

The catalytic triads of CD1 and CD2 determined by analogy with α amylase (7) are present in the following positions:
(Asp 527/Glu 565/Asp 638 for CD1 and Asp 2210/Glu 2248/Asp 2322 for CD2).

Other conserved residues were identified as being important for enzymatic activity: the residues Trp 425/Glu 430 for CD1 and Trp 2122/Glu 2127 for CD2, which are analogous to those of the N-terminal domain of GFT1 described by Monchois et al (4): Trp 344/Glu 349.

In contrast, certain sequences located in the conserved region of the glycosyltransferases and dextransucrases are not found in the CD2 of DSR-E. Thus, as indicated in FIG. 5 below, the sequences FIHNDT (SEQ ID NO: 35) (2214-2220) and KGVQEKV (SEQ ID NO: 36) (2323-2329) diverge from other consensus sequences of dextransucrases already studied, which are respectively NVDADLL (SEQ ID NO: 37) and SEVQTVI (SEQ ID NO: 38).

d) Glucan Binding Domain:

When the DSR-E sequence is compared with known sequences, it appears that the glucan binding region is substantially longer. In fact, the length of this domain is about 500 amino acids in the glycosyltransferases and dextransucrases being studied while in DSR-E, it represents 836 amino acids. Several A and C repeat motifs, in particular a series of AC repetitions, have been identified. Table III below shows the consensus sequences of the repeat motifs of GBD, in particular the A and C motifs, described in the literature relating to dextransucrases of *Leucononstoc* and *Streptococcus* spp.

Identification and Characterization of Enzymatic Activity

Using a glucose acceptor molecule, the dextransucrases produced by recombinant *E. coli* were compared with those produced by *L. mesenteroides* NRRL B-1299.

HPLC analysis of the reaction products with recombinant DSR-E (FIG. 6) showed retention times corresponding to the previously identified GOSs R4 and R5 (2). Type R oligosaccharides are linear GOS series, the α(1→2) bond being linked to the non-reducing end. The OD series, linear GOSs resulting from glycoside α(1→6) bonds with a maltose residue at the reducing end was observed in very small quantities. Three novel compounds, in contrast, were detected in the recombinant enzyme products.

Identification of GOSs Produced:

Finally, FIG. 6b clearly shows that peaks 5 and 7 representing the GOSs of the R series are relatively larger with the recombinant enzyme than with the native enzyme in which the peaks corresponding to panose and OD5 are larger.

EXAMPLE 4

Effect of Deletion of CD2 on the Enzymatic Activity of DSR-E

The genomic DNA of *L. mesenteroides* NRRL B-1299 was used as a matrix to amplify the dsrE gene by PCR deleted from the sequence corresponding to the second catalytic domain. To this end, 2 oligonucleotides, ECHO-dir (5'-AGT-TGTATGAGAGACATGAGGGTAATTTGT-GACCGTAAAAAATTG) (SEQ ID NO: 48) corresponding to the nucleotide sequence -6 to 39 and containing the translation initiation codon, and ECHO-inv-del (5'-GTATTAGT-GAATAAGTATTCACCATTGCATT-TATCGTCAAAATAGTACG) (SEQ ID NO: 49) complementary to the sequence 5889-5937 and corresponding to the peptide sequence YYFDDKGNGEYCFTNT (SEQ

TABLE 3

SEQ ID NOS: 39-43

| Motif | Consensus sequence |
|---|---|
| A | WWYFNxDGQAATGLQTIDGQTVFDDNGxQVKG |
| B | VNGKTYYFGSDGTAQTQANPKGQTFKDGSGVLRFYNLEGQYVSGSGWY |
| C | DGKIYFFDPDSGEVVKNRFV |
| D | GGVVKNADGTYSKY |
| N | YYFxAxQGxxxL | x: any amino acid

EXAMPLE 3

Expression of dsrE in *E. coli*

E. coli BL21 (DE3) pLysS pCR-T7-dsrE cells were cultivated as described above. After polyacrylamide gel electrophoresis (page-SDS), analysis of the protein extracts effectively revealed the presence of several bands having saccharase dextran activity, said activity being measured as described above.

The *E. coli* JM109 [pCR-T7-dsrD] line was deposited at the CNCM on 15th Mar. 2001 with accession number I-2649.

ID NO: 44), were synthesized, to fuse the C-terminal end of the deleted protein with a His tag present on the cloning vector. The PCR reaction was carried out using a DNA thermal cycler model 2400 (Perkin Elmer) with the Expand Long Template System (Boehringer Mannheim) using the following temperature cycle: 94° C. for 3 min, then 25 cycles with: 30 s at 94° C., 30 s at 55° C. and 7 min at 68° C. The PCR product was then cloned into the pUNI donor vector and the resulting plasmid was used in a recombination reaction with the pCR-T7-ΔdsrE expression vector.

The cell extract, preparation, enzymatic reaction and reaction product analysis were those described in Example 3 above.

The HPLC profile of the GOSs obtained with the DSR-E enzyme deleted from the CD2 domain appear in FIG. 6c).

The type R GOS shown as peaks 5 and 7 shown in FIGS. 6a) and 6b) are entirely absent from the products obtained with the recombinant enzyme deleted from CD2. The only analyzable products were those corresponding to linear oligosides resulting from α(1→6) bonds with a maltose residue in the reducing portion. This result clearly indicates the essential role of the catalytic domain located in the carboxy-terminal portion of the enzyme in its capacity to form α(1→2) osidic bonds.

EXAMPLE 5

Study of Structure-function Relationships of DSR-E Protein

The dsrE gene, insofar as it is the first gene encoding a dextransucrase catalyzing the synthesis of α(1→2) bonds to have been cloned, is of particular interest. Thus, it is important to characterize this gene and its expression product, in this case by determining the roles of the different domains making up the DSR-E protein in the function which has been assigned thereto, namely to correspond to a α(1→2) specific to the synthesis of α(1→2) bonds.

5.1 Deleted forms of DSR-E Protein:

A study of six different forms obtained by deletion of one or more domains from the DSR-E protein was envisaged in order to determine the following by reference to FIG. 1 below: (i) the influence of the presence of the CD2 domain by studying GBD-CD2 and Δ(CD2) constructions; (ii) the influence of the presence of the variable zone by analyzing the Δ(ZV) and CD1-GBD forms; and (iii) the intrinsic catalytic potential of the CD1 and CD2 domains expressed in an isolated manner (CD1 and CD2 constructions).

The catalytic activity of each of the different forms was compared with that observed with the control corresponding to the entire form deleted from the single signal peptide Δ(PS) [FIG. 1c)].

5.2 Analysis of Constructions:

At the end of the experimental PCR amplification and cloning procedure detailed above, several clones with an insertion in the expected orientation were obtained for each of the envisaged constructions, with the exception of the truncated GBD-CD2 form for which the desired amplification product could not be cloned.

The sequences for the insertions were determined in order to ensure the absence of mutations that after translation may modify the amino acids located at positions presumed essential for the enzymatic activity of the protein encoded this way.

A mutation was identified at the $31^{st}$ insertion base relative to the control Δ(PS), inducing substitution of one aspartic acid by an asparagine in position 10 of the variable zone. As it is not located in the repeat motifs S of the variable zone (FIG. 4), it appears that the incidence of this mutation on the finally observed function is negligible.

A mutation was introduced into the amplification product corresponding to the construction Δ(CD2), modifying the aromatic residue F1411 in leucine. This mutation was located in the first third of the glucan binding domain GBD at a junction between two repeat motifs.

Because of the errors made by polymerase during PCR amplification, the construction Δ(ZV) did not have the expected sequence. In fact, the insertion contained an open reading frame, that frame essentially corresponding to the GBD-CD2 form which could not be cloned. However, in the GBD-CD2 form obtained definitively in place of Δ(ZV), 46 N-terminal residues were absent. Now, the GBD domain has more than 800 amino acids forming a concatenation of 24 repeat units. This concatenation is such that, over the 46 truncated residues, only the last 9 were located at one of said units, in particular at the first thereof. It thus appears plausible to consider that deletion of these amino acids has no influence on the enzymatic reaction catalyzed by the corresponding protein form. This hypothesis supported by the fact that in other dextransucrases, the loss of a certain number of repeat units from the GBD domain does not significantly reduce the activity of the resulting protein.

The insertion encoding the CD1-GBD form contained a mutation affecting the F633 residue located in the CD1 domain and more precisely in the region that is highly conserved in dextransucrases, itself located just in front of the second aspartic acid of the catalytic triad (FIG. 5). The expected phenylalanine was substituted by a leucine. It is difficult at this stage to estimate the impact of such a mutation on the observed catalytic activity.

The sequence of insertions encoding the catalytic domains CD1 and CD2 was determined in the same manner as for the other constructions.

5.3 Expression Products and Enzymatic Activities

The proteins corresponding to the various deleted forms of DSR-E were expressed by subjecting the recombinant E. coli cells to induction by L-arabinose in a concentration of 0.002%. The enzymatic activity was observed for the first four hours following induction.

The protein extracts obtained by sonication of the cell residues were analyzed by SDS-PAGE electrophoresis (Sambrook and Russel, 2001, supra). The molecular masses of the recombinant proteins were estimated from the electrophoretic profiles obtained, said masses essentially corresponding to the expected masses taking into account the 12 kDa incrementation linked to the thioredoxin tag. Table IV below summarizes the estimated values for the molecular masses of the different truncated forms and, by way of comparison, provides the expected masses.

TABLE IV

| Protein form | Expected mass (kDa) | Expected mass + thioredoxin (kDa) | Estimated mass (kDa) |
|---|---|---|---|
| Δ(PS) | 309 | 321 | 324 |
| Δ(CD2) | 218 | 230 | ND |
| GBD-CD2 | 224 | / | 233 |
| CD1-GBD | 193 | 205 | 199 |
| CD1 | 99 | 111 | 111 |
| CD2 | 95 | 107 | ND |

ND: not determined

Table V below indicates the nature and position of amino acids marking the start and end of the protein forms constructed in this study. The different positions refer to SEQ ID No: 2 corresponding to the protein DSR-E.

TABLE V

| Protein form | Starting amino acid | Ending amino acid | Total length |
|---|---|---|---|
| Δ(PS) | N41 | I2835 | 2795 |
| Δ(CD2) | M1 | L1980 | 1980 |
| GBD-CD2 | M1188 | I2835 | 1648 |
| CD1-GBD | I248 | L1980 | 1733 |
| CD1 | I248 | Q1141 | 894 |
| CD2 | D1981 | I2835 | 855 |

The GBD-CD2 form did not have a thioredoxin tag. In fact, this form was derived from experimental uncertainty occasioned by the procedure for PCR amplification of the sequence assumed to encode the Δ(ZV) form. Because of the deletions from the sequences thus generated, the thioredoxin tag, in principle situated at 5' from the protein of interest, could not be fused with the GBD-CD2 region.

The quality of the electrophoresis gels did not allow determination as to whether the level of expression of the different forms was quantitatively identical and as a result whether said forms were present in the same proportions in the cell extracts.

The activity measurements provided were established on the basis of a given volume of cell extracts but could not be extrapolated to the quantity of each protein actually contained in said volume of extracts.

The synthesis of dextran polymers in situ by incubating electrophoresis gels in a saccharose solution and subsequent staining with Schiff's reagent confirmed the presence of proteins having a glucan-saccharase activity in cell extracts corresponding to Δ(PS), Δ(CD2), GBD-CD2 and CD1-GBD.

Table VI below shows the maximum enzymatic activities observed for each construction. The results confirm the data drawn from the experiments in which the gels were stained with Schiff's reagent, namely the fact that the cell extracts relative to the forms Δ(PS), Δ(CD2), GBD-CD2 and CD1-GBD had a saccharase activity, in contrast to the two catalytic domains taken in isolation. This result was in agreement with the literature, given that it has been demonstrated that in other dextransucrases, the absence of the GBD domain induced a drastic loss of enzymatic activity (8, 9, 10).

TABLE VI

| Protein form | Δ(PS) | Δ(CD2) | GBD-CD2 | CD1-GBD | CD1 | CD2 |
|---|---|---|---|---|---|---|
| maximum activity (U/l) | 1063 | 181 | 86 | 235 | 5.3 | 0 |

The intrinsic activity of the CD1 form was too low to be detected. Regarding the GBD-CD2 form, it had a non negligible activity which leads to the conclusion that the corresponding structural organization, namely a catalytic domain downstream of the glucan binding domain, remains enzymatically active.

5.4 Effect of Deletions on Oligoside Synthesis:

Provided that the specificity of the synthesis of α(1→2) bonds was conserved during the reaction in the presence of an acceptor, experiments for synthesizing oligosides starting from maltose were carried out (FIG. 7).

When the reactions were carried out to completion, i.e. all of the saccharose had been consumed, the oligoside synthesis yields were calculated. The results are shown in Table VI below. Only the reaction involving the cell extract containing the protein form CD1 did not allow such a calculation. The temperature effect probably resulted in inactivation of the very low activity present in the protein extract.

TABLE VII

| Protein form | Yield of oligosides in OD series (%) | Yield of oligosides in R series (%) | Total oligoside yield |
|---|---|---|---|
| Native enzyme | 36 | 28 | 64 |
| Δ(PS) | 41 | 14 | 55 |
| Δ(CD2) | 67 | 1 | 68 |
| GBD-CD2 | 45 | 47 | 92 |
| CD1-GBD | 100 | 0 | 100 |

As indicated in FIG. 7 below, the presence of oligosides from series R was only detected with enzymatic forms having the catalytic domain CD2, with the exception of the case in which said domain was isolated and then rendered completely inactive. In fact, the retention time for the oligosides synthesized by the deleted form of the second catalytic domain and by the CD1-GBD form corresponded only to those in the OD series, i.e. to GOSs deprived of α(1→2) bonds. These results thus indicate that the CD2 domain was required for the formation of α(1→2) bonds.

The products obtained with the GBD-CD2 form have supported these observations. This construction, which had CD2 as the only catalytic domain, was capable of catalyzing in a preponderant manner the synthesis of oligosides from the R series, having α(1→2) bonds. Thus, this results demonstrates that specificity in terms of the function of the DSR-E enzyme resides in the highly original sequence for this domain, and not in the association of two catalytic domains. Further, the GBD-CD2 protein form also allowed the synthesis of α(1→6) bonds. However, the low yields obtained for these oligosides indicated that they were preferentially converted into oligosides with a higher degree of polymerization belonging to the R series, which prevented their accumulation in the reaction medium, differing from molecules from the R series which were not converted (2).

By comparing the profiles of the products obtained as shown in FIG. 7, it is clear that the entire form Δ(PS) mainly synthesizes linear oligosides. In fact, the molecule R4 was absent and the oligoside R5 only present in a small amount. The catalytic domain CD1 catalyzed the exclusive synthesis of α(1→6) bonds and its activity appeared to be preponderant with respect to that of the CD2 domain. In addition, in the entire form of the enzyme, the implication of the CD2 domain would thus be less important because of: (i) lower intrinsic catalytic parameters; and/or (ii) a global enzyme configuration that was unfavorable to its activity.

Further, the entire enzyme Δ(PS) catalyzed the synthesis of oligosides from the R series with a lower yield than that observed with the mixture of dextransucrases produced by *L. mesenteroides* NRRL B-1299 (FIG. 7). The yield obtained, 28%, was situated between those observed for the entire form Δ(PS) and for the GBD-CD2 form. It is known that the wild strain produces several forms of dextransucrases that are susceptible of synthesizing osidic bonds, in particular α(1Δ2) bonds. One hypothesis has been proposed, in which said forms are the degradation products of DSR-E. Insofar as the truncated forms of DSR-E such as GBD-CD2 could catalyze the synthesis of oligosides from the R series more effectively, it would appear that the yields obtained with the heterogeneous mixture produced by *L. mesenteroides* NRRL B-1299 can be attributed to the contribution of the catalytic activities of the ensemble of said different enzymatic forms.

In conclusion, by isolating a particular dextransucrase produced by *L. mesenteroides*, the inventors have succeeded in characterizing a particular and unexpected structure of this enzyme that can produce oligosides of interest and have α(1→2) type linkages. Identification and characterization of this sequence allows the construction of recombinant cells or organisms specifically expressing this enzyme and also allows its modification by directed or random mutagenesis or by DNA shuffling to further improve its characteristics to be envisaged.

This invention can also improve the yield and reproducibility of the production of GOSs of interest for the different applications cited above.

REFERENCES (1) Monchois V., Willemot R. M., Monsan P. (1999). Glucan-sucrases: mechanism of action and structure-function relationships. FEMS microbiol. Rev. 23,131-151.
(2) Dols M., Remaud-Simeon M., Willemot R. M., Vignon M. R., Monsan P. F. (1998). Structural characterization of the maltose acceptor-products synthesised by *Leuconostoc mesenteroides* NRRL B-1299 dextransucrase. Carbohydrate Research 305, 549-559.
(3) Arnold F. H. (2001). Nature 409 n° 6817, 253.
(4) Monchois V. Vignon M., Russel R. R. B. (1999). Isolation of key amino-acid residues at the N-terminal end of the core region of *Streptococcus* downei glucansucrase GTF-I. Appl. Microbiol. Biotechnol. 52, 660-665.
(5) Wilke-Douglas M., Perchorowicz J. T., Houck C. M., Thomas B. R. (1989). Methods and compositions for altering physical characteristics of fruit and fruit products. PCT patent, WO 89/12386.
(6) Arguello-Morales M. A., Remaud-Simeon M., Pizzut S., Sarcabal P., Willemot R. M., Monsan P. (2000). Sequence analysis of the gene encoding alternansucrase, a sucrose glucosyltransferase from *Leuconostoc mesenteroides* NRRL B-1355. FEMS Microb. Lett. 182, 81-85.
(7) Devulapalle K. S., Goodman S., Gao Q, Hemsley A., Mooser G. (1997). Knowledge-based model of a glusocyltransferase from oral bacterial group of mutant streptococci. Protein Sci. 6, 2489-2493.
(8) Kato C., and Kuramitsu H. K. (1990). Carboxy-terminal deletion analysis of the *Streptococcus mutans* glucosyltransferase-1 enzyme. FEMS Microbiol. Lett. 72, 299-302.
(9) Lis M., Shiroza T., et Kuramitsu H. K. (1995). Role of the C-terminal direct repeating units of the *Streptococcus mutans* glucosyltransferase-S in glucan binding. Appl. Env. Microbiol. 61, 2040-2042.
(10) Monchois V., Remaud-Simeon M., Russel R. R. B., Monsan P. and Willemot R. M. (1997). Characterization of *Leuconostoc mesenteroides* NRRL B-512F dextransucrase (DSR-S) and identification of amino-acid residues playing a key role in enzyme activity. Appl. Microbiol. Biotechnol. 48, 465-472.

What is claimed is:

1. An isolated nucleic acid comprising SEQ ID NO:4 or its full length complementary strand.

2. An isolated nucleic acid comprising:
   a) sequence encoding a dextransucrase expressed by the plasmid pCR-Ty-dsrD deposited at the CNCM with accession number I-2649; or
   b) a full length complementary sequence to the sequence in a).

3. An expression vector comprising a nucleic acid according to claim 1 or claim 2.

4. The expression vector according to claim 3, in which the nucleic acid is under the control of a sequence allowing its expression in prokaryotic or eukaryotic cells.

5. A host cell transformed by a nucleic acid according to claim 1.

6. A host cell transformed by a vector according to claim 3.

7. The transformed host cell according to claim 5, selected from the group comprising *E. coli, Leuconostocci*, plants, *Lactococci* and *Bacilli* or yeasts.

8. The transformed host cell according to claim 7, wherein said transformed host cell is a strain of *E. coli* deposited at the CNCM with accession number I-2649.

9. An isolated nucleic acid encoding an enzyme with glycosyltransferase activity that can form dextrans having α(1→2) linkages from saccharose, α-D-fluoroglucose, paranitrophenyl-α-D glucopyranoside, α-D-glucopyranoside-α-D sorbofuranoside or 4-O-α-D galactopyranosylsucrose and comprising at least one nucleotide sequence encoding a catalytic domain of SEQ ID NO:3 and located 3' of a sequence encoding a glucan binding domain.

10. An isolated nucleic acid consisting of SEQ ID NO:4 or its full length complementary strand.

11. A host cell transformed by a nucleic acid according to claim 9.

12. A host cell transformed by a nucleic acid according to claim 2.

13. A host cell transformed by an expression vector according to claim 4.

14. The isolated nucleic acid molecule according to claim 9, wherein the nucleotide sequence encoding the glucan binding domain is between two nucleotide sequences encoding the catalytic domains.

* * * * *

UNITED STATES PATENT AND TRADEMARK OFFICE
CERTIFICATE OF CORRECTION

| | | |
|---|---|---|
| PATENT NO. | : 7,439,049 B2 | Page 1 of 1 |
| APPLICATION NO. | : 10/509024 | |
| DATED | : October 21, 2008 | |
| INVENTOR(S) | : Sophie Anne Michèle Bozonet et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1,131 days.

Signed and Sealed this
Twenty-second Day of April, 2014

Michelle K. Lee
*Deputy Director of the United States Patent and Trademark Office*